(12) United States Patent
Laufer et al.

(10) Patent No.: US 8,052,672 B2
(45) Date of Patent: Nov. 8, 2011

(54) FAT REMOVAL AND NERVE PROTECTION DEVICE AND METHOD

(75) Inventors: Michael D. Laufer, Menlo Park, CA (US); Hien Nguyen, Fountain Valley, CA (US); Suresh K. Wadhwani, Mission Viejo, CA (US); Payam Adlparvar, Lake Forest, CA (US); Bruce Stambaugh, Anaheim, CA (US); Tony R. Brown, Anaheim Hills, CA (US)

(73) Assignee: LENR Solutions, Inc.

( * ) Notice: Subject to any disclaimer, the term of this patent is extended or adjusted under 35 U.S.C. 154(b) by 1881 days.

(21) Appl. No.: 10/735,349

(22) Filed: Dec. 11, 2003

(65) Prior Publication Data

US 2005/0165345 A1    Jul. 28, 2005

Related U.S. Application Data

(63) Continuation-in-part of application No. 10/658,588, filed on Sep. 8, 2003, now abandoned, which is a continuation of application No. 09/874,360, filed on Jun. 6, 2001, now Pat. No. 6,626,890.

(51) Int. Cl.
*A61M 1/00* (2006.01)
*A61B 17/32* (2006.01)

(52) U.S. Cl. ................................ 604/542; 606/170
(58) Field of Classification Search .............. 604/542, 604/540, 902; 606/170
See application file for complete search history.

(56) References Cited

U.S. PATENT DOCUMENTS

| | | | |
|---|---|---|---|
| 4,735,605 A | 4/1988 | Swartz | |
| 4,867,157 A | 9/1989 | McGurk-Burleson et al. | |
| 4,932,935 A | 6/1990 | Swartz | |
| 5,569,178 A | 10/1996 | Henley | |
| 5,823,990 A | 10/1998 | Henley | |
| 5,906,609 A | 5/1999 | Assa et al. | |
| 6,071,260 A * | 6/2000 | Halverson | 604/22 |
| 6,503,263 B2 * | 1/2003 | Adams | 606/170 |
| 6,626,890 B2 * | 9/2003 | Nguyen et al. | 604/542 |
| 2003/0176851 A1 * | 9/2003 | Bass | 604/542 |

* cited by examiner

*Primary Examiner* — Jacqueline F. Stephens

(57) ABSTRACT

A fat removal device includes a screen which includes passages through which fat can be extruded, to be cut or melted away from the surface of an internal organ. The device includes a blade to cut the fat or radiofrequency monopolar or bipolar electrodes to melt the fat, aspiration to remove the fat away from the screen and blade, irrigation to irrigate the screen and blade, and an electrocautery member to cauterize the capillary bed of the fat. Methods of using removing the fat layer from the surface of an internal body organ are also described.

27 Claims, 31 Drawing Sheets

FAT REMOVAL AND NERVE PROTECTION DEVICE AND METHOD

RELATED APPLICATION

This application is a continuation-in-part of U.S. application Ser. No. 10/658,588, filed on Sep. 8, 2003; now abandoned which is a continuation of U.S. application Ser. No. 09/874,360, filed Jun. 6, 2001, which is now issued U.S. Pat. No. 6,626,890.

BACKGROUND OF THE INVENTION

1. Field of the Invention

The present invention relates to apparatus and methods for removing fatty tissue from a human body without damaging underlying nerves.

2. Brief Description of the Related Art

Recent advances in cardiology, radiology, cardiothorasic vascular and neuro surgery have allowed patients suffering from various diseases of the internal organs to benefit from less invasive techniques to surgically treat their conditions. With the advent of newer techniques, however, come newer difficulties in the application of these techniques to all the qualified patients.

Recent advanced techniques and devices allow for the correction of numerous defects of the internal organs, e.g., the heart, by access to the surface of the organs. For example, performing coronary artery bypass surgery on a beating heart has been used to treat coronary artery disease, attaching leads to the exterior surface of the heart to collect diagnostic data and to pace the heart, or performing atrial fibrillation procedures. In all of these procedures, however, often a thick layer of fatty tissue must be removed from around the heart to expose the myocardial tissue to be treated. To further complicate the procedure, the fatty layer may be enveloped in a tougher layer of connective tissue, the pericardium, which must first be incised to expose the fat underneath. Furthermore, the vasculature which provide blood to the heart itself, the coronary arteries and veins, may be located on the exterior of the cardiac tissue and under and in the fat. The coronary arteries and cardiac veins traverse the myocardial surface, supplying oxygenated blood and conducting deoxygenated blood away from the cardiac tissues, respectively. Typically, the pericardium is cut with a scalpel to expose the fat underneath, which in turn is incised with a scalpel to expose the surface of the heart to perform a procedure, e.g., bypass surgery, pacing lead attachment, atrial fibrillation procedures, etc. The use of a scalpel to remove the fat clearly presents a level of danger to the patient's coronary arteries which is only marginally tolerable; the consequences of mishap are severe.

The fat layer is generally a semi liquid form at body temperature. At elevated temperatures the fatty tissue will become more liquified. The cell membranes of the fat tissue can be ruptured when they are mechanically stressed, which will allow the fat contents of the cell to flow freely.

Prior devices exist which aspirate fat or other substances from the body of a patient, but which are not suitable for removing the fat layer from the external surface of an internal body organ. Laparoscopes exist, but are not useful because they cannot break up fatty tissue while ensuring that larger blood vessels which are located under the fat are not also severed. Numerous atherectomy devices have been proposed, however they are far too small to be effectively employed to remove the sometimes large volumes of fat which covers the organ, and also do not provide any protection for the underlying nerves and blood vessels.

Protecting the underlying nerves from damage is especially important. For example, in thoracic surgery as well as in other surgical procedures, identification of nerves is critical. Failure to identify nerves during surgery could result in those nerves being inadvertently damaged. Nerves are often enclosed or covered with fat, making their identification and isolation particularly difficult. Generally, those skilled in the art must identify nerves by slowly dissecting with scissors and forceps. Failure to identify nerves can lead to severe disability should those nerves be injured as a result. Injuries include numbness as well as the inability to move. Frequently, these injuries are permanent.

Within dermatology and plastic surgery, the inner surface of the skin is aspirated for fat. Nerves and vessels that are in the same space can be easily damaged. Identification of these vessels and nerves prior to injury is important.

Within thoracic, neurosurgery and vascular surgery, procedures to isolate parts of a nerve in order to create therapeutic benefit are becoming increasingly common. For example, stellate ganglion procedures for hyperhydrosis (i.e. excessive sweating) require careful dissection, identification and treatment of the ganglion. If it were possible to identify and isolate the nerve more quickly, these procedures would be safer and faster to do. Therefore there is a need for an innovative device that allows the surgeon to separate underlying nerves from their covering fat. Such a device is herein disclosed.

Another commonly performed procedure is liposuction, usually performed for cosmetic improvement. Frequently, nerve damage occurs due to nerves being injured by the suction device The invention herein described would be beneficial to identifying nerves prior to injury and also would aid in the removal of fat without associated nerve injury.

SUMMARY OF THE INVENTION

In accordance with a first exemplary embodiment of the present invention, a fat removal and nerve protection device comprises a cannula having a longitudinal axis, a proximal end, a distal end, a lumen extending proximally along said longitudinal axis, and an opening in said cannula at said distal end which fluidly communicates said lumen with the exterior of said cannula, and a protective mesh attached to said distal end and distal of said opening, said mesh including openings sized to permit human fat cells to extrude through said openings when said mesh is pressed against a mass of human fatty tissue, said openings also sized to prevent human nerves underlying said human fatty tissue from passing through said openings when said mesh is pressed against said mass of human fatty tissue.

In accordance with a second exemplary embodiment of the present invention, a fat removal and nerve protection device comprises a cannula having a longitudinal axis, a proximal end, a distal end, a lumen extending proximally along said longitudinal axis, and an opening in said cannula at said distal end which fluidly communicates said lumen with the exterior of said cannula, and an energy transmitting wire located in said cannula and including a tip distal of said cannula distal end, said wire and tip being longitudinally movable at a frequency and magnitude which at least partially disrupts the cell walls of said human fat cells.

In accordance with a third exemplary embodiment of the present invention, a fat removal and nerve protection device comprises a cannula having a longitudinal axis, a proximal end, a distal end, an outer diameter R, a lumen extending proximally along said longitudinal axis, and an opening in said cannula at said distal end which fluidly communicates said lumen with the exterior of said cannula, and a cutting element in said lumen adjacent said cannula distal end, said cutting element spaced from said cannula distal end a distance D, wherein R and D are together selected to permit human fat cells to extrude into said cannula opening when said cannula distal end is pressed against a mass of human fatty tissue, R and D are together selected also being sized to prevent human nerves underlying said human fatty tissue from passing into said cannula opening when said cannula distal end is pressed against said mass of human fatty tissue.

In accordance with a fourth exemplary embodiment of the present invention, a fat removal and nerve protection device comprises a cannula having a longitudinal axis, a proximal end, a distal end, a tip at said distal end, a lumen extending proximally along said longitudinal axis, and an opening in said cannula at said distal end which fluidly communicates said lumen with the exterior of said cannula, said cannula tip being angled inward, and a cutting element in said lumen adjacent said cannula distal end, wherein said cannula tip angle is selected to permit human fat cells to extrude into said cannula opening when said cannula distal end is pressed against a mass of human fatty tissue, said cannula tip angle also being selected to prevent human nerves underlying said human fatty tissue from passing into said cannula opening when said cannula distal end is pressed against said mass of human fatty tissue.

In accordance with a fifth exemplary embodiment of the present invention, a fat removal and nerve protection device comprises a cannula having a longitudinal axis, a proximal end, a distal end, a closed tip at said distal end, a lumen extending proximally along said longitudinal axis, and an opening in said cannula proximal of said distal end which fluidly communicates said lumen with the exterior of said cannula, a rotatable shaft in said cannula, a blade attached to said rotatable shaft adjacent said opening, wherein when said cannula opening is pressed against a mass of human fatty tissue, and when said rotatable shaft is caused to rotate, said blade rotates and cuts fatty tissue which has extruded through said opening, said cannula opening being sized to prevent human nerves underlying said human fatty tissue from passing into said cannula opening when pressed against said mass of human fatty tissue.

In accordance with a sixth exemplary embodiment of the present invention, a fat removal and nerve protection tool for removing fat comprises a screen having at least one passageway sized to allow fat cells to extrude through the screen while preventing nerves from passing through said screen, and a separate cutting member positionable adjacent to said screen to cut fat which has been extruded through said screen passageway.

In accordance with a seventh exemplary embodiment of the present invention, a fat removal and nerve protection tool for removing fat comprises a handle having a proximal end, a distal end, and a hollow interior, a screen at said handle distal end, said screen including at least one passage therethrough, a rotatable blade in said handle and immediately proximal of said screen, and a rotatable shaft attached to said blade and extending proximally from said rotatable blade.

In accordance with an eighth exemplary embodiment of the present invention, a fat removal and nerve protection tool for removing fat comprises a screen having at least one passageway sized to allow fat cells to extrude through the screen while preventing nerves from passing through said screen, and a cutting member adjacent to said screen and movable over said screen to cut fat which has been extruded through said screen passageway.

In accordance with a ninth exemplary embodiment of the present invention, a method of removing fat while preventing underlying nerve damage comprises the steps of exposing a portion of said fat layer, pressing said fat layer with a surface having at least one hole, extruding fat through said at least one hole, and cutting said fat that has extruded through said hole on a side of said surface opposite said fat layer.

In accordance with a tenth exemplary embodiment of the present invention, a method of removing fat while preventing underlying nerve damage comprises the steps of exposing a portion of said fat, pressing said fat with a surface which vibrates at a frequency and magnitude sufficient to rupture cell walls contained in said fat, and aspirating fatty tissue.

In accordance with an eleventh exemplary embodiment of the present invention, a fat removal and nerve protection tool comprises two bipolar wires each having a cross-sectional diameter and a centerline, each bipolar wire having a cross-sectional diameter from about 0.150 inches to about 0.045 inches, the two bipolar wires spaced from each other at a centerline-to-centerline distance from about 0.040 inches to about 0.200 inches.

In accordance with a twelfth exemplary embodiment of the present invention, a fat removal and nerve protection tool comprises a first outer sheath electrode having a lumen and a distal end, the outer sheath electrode including holes at the distal end to allow fat to enter the lumen, and a second helical wireform inner rotatable electrode positioned in the lumen to rotate relative to the holes to move to the proximal end of the tool any fat that is melted upon application of radio frequency energy between the first and second electrodes such that a vacuum source can remove the fat from the tool. In addition, the helical member may be formed with a convexity so that, when rotated, it creates a suction within the canula to move fat into the canula Still other objects, features, and attendant advantages of the present invention will become apparent to those skilled in the art from a reading of the following detailed description of embodiments constructed in accordance therewith, taken in conjunction with the accompanying drawings.

BRIEF DESCRIPTION OF THE DRAWINGS

The invention of the present application will now be described in more detail with reference to preferred embodiments of the apparatus and method, given only by way of example, and with reference to the accompanying drawings, in which.

DESCRIPTION OF THE PREFERRED EMBODIMENTS

Figure 1:
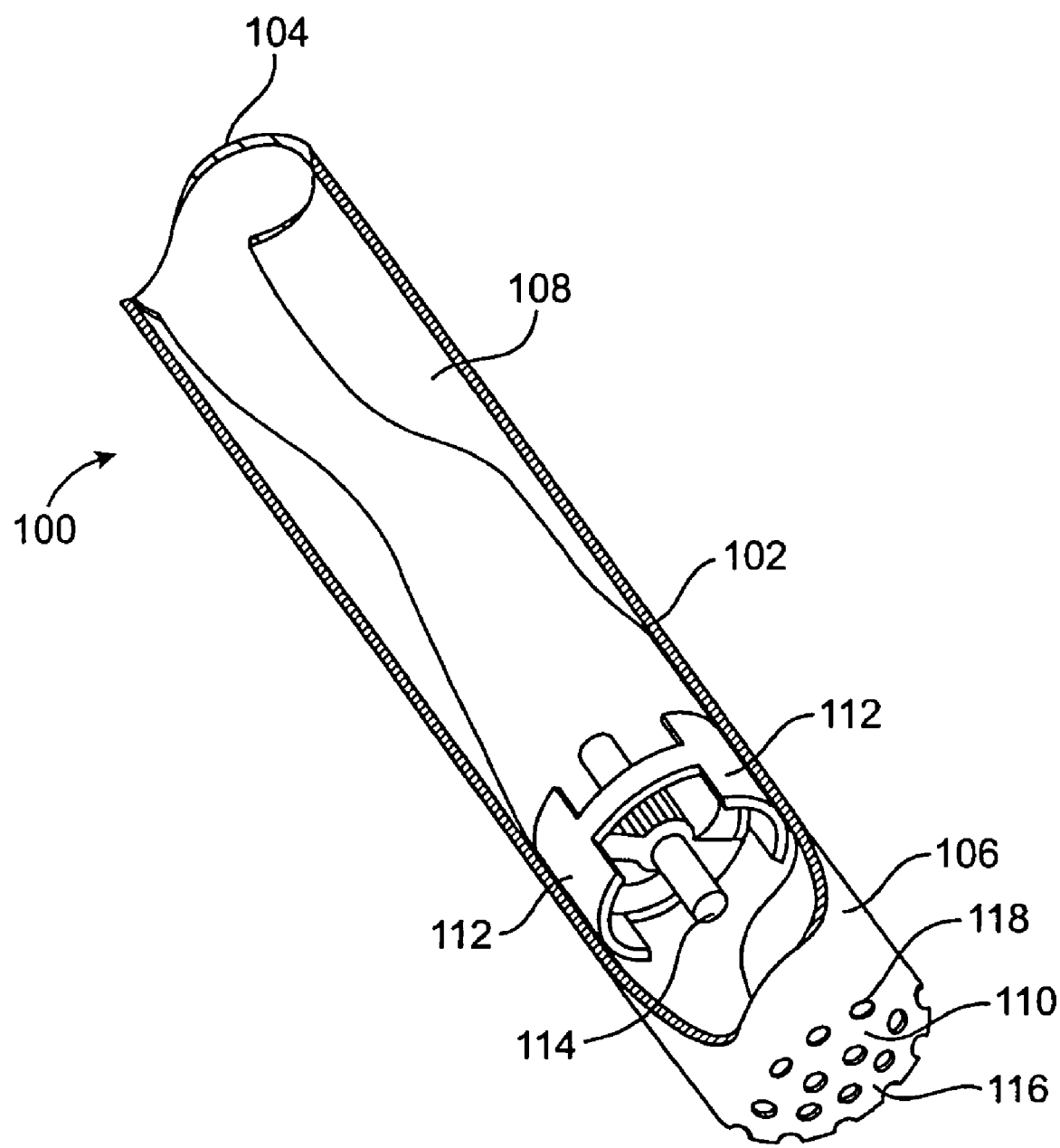
FIG. 1 illustrates a cross-sectional view of a first exemplary embodiment in accordance with the present invention.

Referring to the drawing figures, like reference numerals designate identical or corresponding elements throughout the several figures.

FIG. 1 illustrates a cross-sectional view of a first exemplary embodiment 100 of a fat removal and nerve protection device in accordance with the present invention. Device 100 includes a cannula 102 including a proximal end 104, a distal end 106, and an aspiration or suction lumen 108 extending between the proximal and distal ends. A source of vacuum (not illustrated) is fluidly connected to lumen 108 to aspirate all the fat and fluid which enters into the lumen. Device 100 further includes a protective mesh 110 extending from or a part of the distal end 106 of the cannula 102, which includes openings 118 of a size preselected to allow fatty tissues and fat cells to extrude through the mesh, while preventing nerves, as well as blood vessels of certain sizes from entering into the cannula, as will be described in greater detail below.

Cannula 102 further includes a source of vibrational energy 112, e.g., an ultrasonic transducer, which supplies vibrational energy to the fatty tissue against which the cannula is pressed. This vibrational energy is conducted at a frequency which is selected to substantially disrupt or otherwise rupture the outer membranes of the cells which make up the fatty tissue. The frequency of operation of the source 112 will vary upon the exact nature of the fatty tissue which is desired to break up. In preferred embodiments, the frequency may range from 500 kHz to 2 MHz. In one preferred embodiment, the frequency is approximately 1 MHz. Cannula 102 further includes a heat radiating element or heater 114, e.g., a resistive heating element, for heating the fatty tissue against which the cannula is pressed. Heat generated by heater 114 aids in breaking up the fatty tissues by the vibrational energy supplied by the source 112, by heating and thereby reducing the viscosity of the contents of the cells ruptured by the vibrational energy supplied by source 112. Together, source 112 and heater 114 are positioned at the distal tip just above holes 118 or mesh 110 generate a cell rupture zone 116 in which the cells of the fatty tissue against which cannula 102 is pressed are ruptured, heated, and aspirated into lumen 108 of the cannula. Furthermore, the heat transfer from heater 114 functions to cauterize the capillary bed which is part of the fatty tissue, thereby minimizing bleeding of the tissue and the chances for infection to set in, and aids in postoperative healing of these tissues. Source 112 and heater 114 are connected to appropriate power sources at the proximal end 104 of the cannula 102 (not illustrated), as will be readily appreciated by one of ordinary skill in the art.

As discussed briefly above, mesh 110 or holes 118 is constructed to allow only the capillary blood vessels of the fatty tissue to enter into the interior of cannula 102, so that the nerves, and larger blood vessels, the exposure of which is the object of the process of removing the fatty tissue layer, will not be harmed by the device 100. For example, in the specific case of nerves, the fat will melt at a lower temperature than the temperature at which the nerves will be damaged. In the case of larger blood vessels, such blood vessels are effected less by the heat from heater 114, as a slight increase in temperature would have little effect on the vessel walls of these larger blood vessels, and they furthermore have a greater heat capacity and ability to conduct heat away from the operative site by blood flowing through them.

The function of the device 100 illustrated in FIG. 1 will now be briefly described. Cannula 102 is pressed up against a mass of fatty tissue, which may include, but is not limited to, the outer fatty tissue layer of an organ the outer surface of which it is desired to access directly. Cannula 102 can be inserted through an appropriately sized endoscope (e.g., thoracoscope), or can be inserted directly via an opening created in the patient's body via full or partial thoracotomy. If an overlying layer of tissue covers the layer of fatty tissue, e.g.

the pericardium, it is cut to expose the underlying fatty tissue. Distal end 106 is pressed against the fatty tissue. Suction is applied to lumen 108, vibrational energy is emitted from source 112, and heat is delivered from heater 114, preferably simultaneously, but optionally in any serial combination. Fatty tissue cells are ruptured by the application of vibrational energy, with the aid of an increase in the temperature of the cells from heater 114, and the contents of the ruptured cells are aspirated through mesh 110 or holes 118, into lumen 108, and proximally through cannula 102. Mesh 110 or holes 118 prevent blood vessels larger than the capillary bed that vascularizes the fatty tissue layer from being drawn into the lumen 108. In optional preferred aspects, the mesh 110 or holes 118 are dimensioned to be small enough such that nerve damage is avoided. For example, holes 118 in mesh 110 may optionally be a diameter from 10% less than the diameter of the nerve to be protected to 6 mm. At such dimensions, mesh 110 or holes 118 would be small enough to prevent nerves from passing therethrough, yet still be large enough to permit the overlying fatty tissue to pass therethrough. The cannular is moved to a new site on the fatty tissue layer when a sufficient amount of the fat has been removed to perform another procedure on the surface of the organ.

Figure 2:
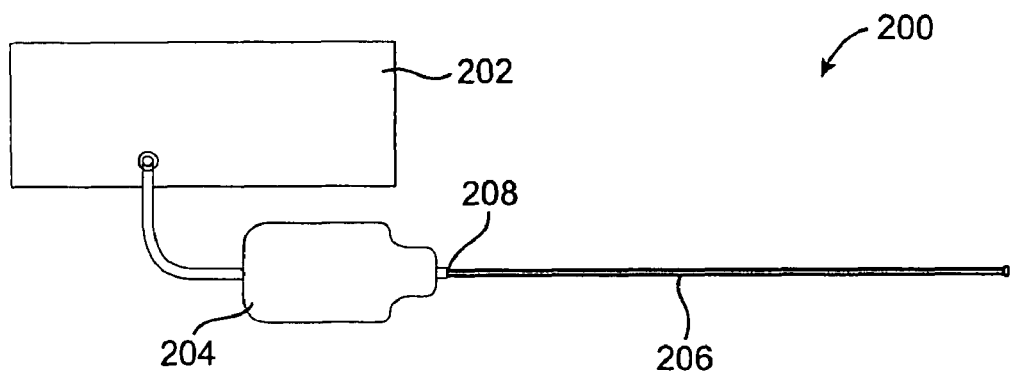
FIG. 2 schematically illustrates a view of a second exemplary embodiment in accordance with the present invention.
Figure 3:
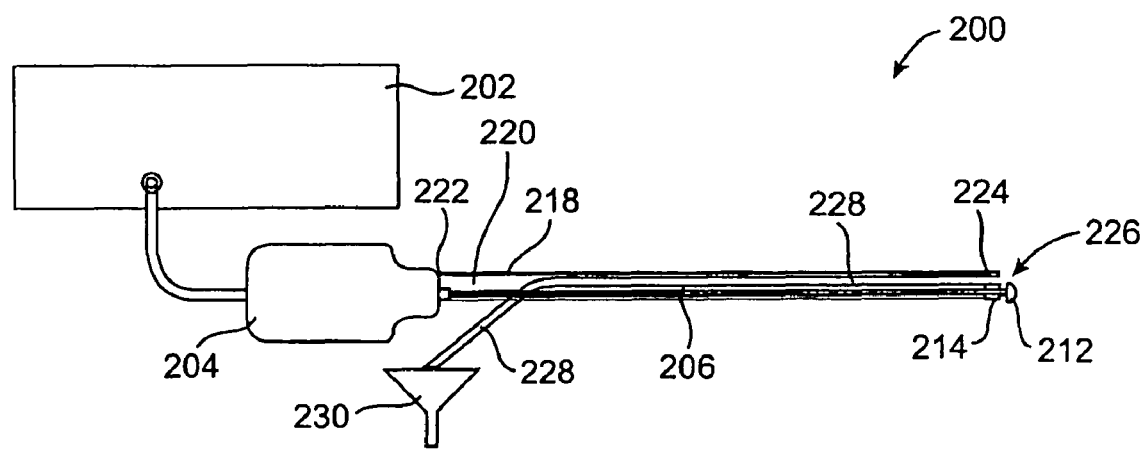
FIG. 3 further illustrates the device of FIG. 2.
Figure 4:
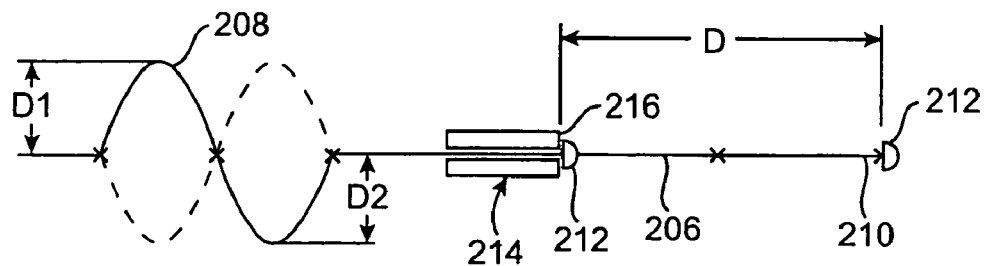
FIG. 4 illustrates portions of the device of FIG. 2.

FIGS. 2-4 schematically illustrate views of a second exemplary embodiment of a fat removal and nerve protection device 200 in accordance with the present invention. Device 200 includes an RF or ultrasonic generator 202 connected to a transducer 204. Transducer 204 causes oscillatory lateral motion of a proximal end 208 of a wire 206. This lateral motion is transformed into longitudinal motion of the distal end 210 of wire 206 by a restraint bushing 214 positioned between the proximal and distal ends of the wire. In the exemplary embodiment illustrated in FIGS. 2-4, bushing 214 is positioned at the distal end of the device 200; however, bushing 214 may be positioned anywhere along the length of wire 206 and still be within the spirit and scope of the invention.

Distal end 210 of wire 206 includes a tip 212, which is preferably enlarged, and more preferably is in the form of a hemisphere, which moves longitudinally to impact against fatty tissue against which the device is pressed. As illustrated in FIG. 4, as generator 202 laterally moves the proximal end 208 of wire 206, the wire sweeps over an area between two sine curves between two maxima $D_1$ and $D_2$. The longitudinal distance D that the distal tip 212 of wire 206 travels between the most proximal and most distal positions satisfies the equation:

$$D=2(D_1+D_2).$$

Wire 206 may be formed of any biocompatible material which is able to transmit the ultrasonic energy from generator 202. Preferably, wire 206 is formed of a nickel-titanium alloy, commonly referred to as Nitinol®, or may be formed of a surgical stainless steel, although other materials can be used, such as platinum, etc. Wire 206 preferably has an outer diameter of about 0.05 inches, although the wire can be formed larger or smaller, to increase or decrease its strength, and to tune the wire to eliminate any higher order, steady state or transient harmonics which may arise by application of the oscillatory motion to the wire, as will be readily apparent to one of ordinary skill in the art.

Device 200 also includes a cannula 218 having a lumen 220 through which wire is inserted. Lumen 220 extends from a proximal end 222 to a distal end 224 of the cannula. Cannula 218 includes an aspiration port 226 at the distal end 224 thereof, which is in fluid communication with an aspiration conduit 228 extending through the wall of the cannula to a source of vacuum and a collection jar 230. Aspiration port 226 is preferably located at the distalmost end of cannula 218; however, the aspiration port can be optionally located on the sidewall of the cannula, or both end and side aspiration ports may be provided to provide additional area through which to aspirate tissue, and to provide a vacuum break if any of the aspiration ports become clogged or otherwise blocked. Bushing 214 is positioned inside lumen 220 to restrain wire 206 and transform the lateral motion of wire 206 into longitudinal motion. Cannula 218 may also optionally include a source of irrigation fluid (not illustrated) in fluid communication with lumen 200, and an irrigation port (not illustrated) adjacent the distal end 224 of the cannula, for supplying irrigation fluid to the distal tip. Irrigation fluid may be optionally supplied to assist in heating, cooling, or selectively heating and cooling the tissue and tip 212.

The function of device 200 and a preferred method of use thereof will now be described with reference to FIGS. 2-4. Two incisions are made under the chest of a patient. The first incision is used to introduce an endoscopic, e.g., laparoscopic, device to view the surface of the organ from which it is desired to remove a layer of fatty tissue, e.g, the heart. The endoscope, which has an external diameter preferably not greater than about 2 mm to about 3 mm and has a focal length between about 1 cm and about 1.5 cm provides detailed images of the surface of the heart regardless the up and down movement of the beating heart. The endoscope is a common device, the details of which will be readily apparent to one of ordinary skill in the art.

A second incision is made to introduce ultrasonic drilling device 200. Ultrasonic generator 202 is coupled to transducer 204 to generate and transmit ultrasonic energy between about 18 KHz and about 20 KHz. A drilling tip 212 is attached to the distal end of wire 206 to increase the area of application of the ultrasonic energy to the fatty tissue.

Wire 206 is now inserted into cannula 218, which has its proximal end 222 connected to transducer 204. When transducer 204 applies its oscillatory energy through wire 206, the wire will vibrate inside the cannula 218. As the distal end 224 of the wire is constrained inside bushing 214, the sine wave motion is transformed into longitudinal or back and forth motion. Because of the particular geometry of device 200, longitudinal displacement of tip 212 occurs at a frequency twice that of the frequency at which generator 202 is operated. This effectively make tip 212 a high-speed drill bit which impacts against fatty tissue against which the tip 212 is pressed, disrupting the cell walls of the tissue in a manner similar to the disruption caused by device 100, described above. Furthermore, the length D of the displacement of the tip 212 can be very closely controlled by changing the frequency at which generator 202 operates, which will change the wavelength of the sine curves illustrated in FIG. 4, and therefore distances $D_1$ and $D_2$.

As fatty tissue is disrupted by the operation of tip 212, the tissue is aspirated through aspiration conduit 228 to jar 230. If desired, irrigation fluid may also be provided to heat the fatty tissue to make the contents of the ruptured cells less viscous. Also, irrigation fluid may be provided to cool the tip 212 in the event that it becomes overheated, and to wash the surgical site.

Figure 6:
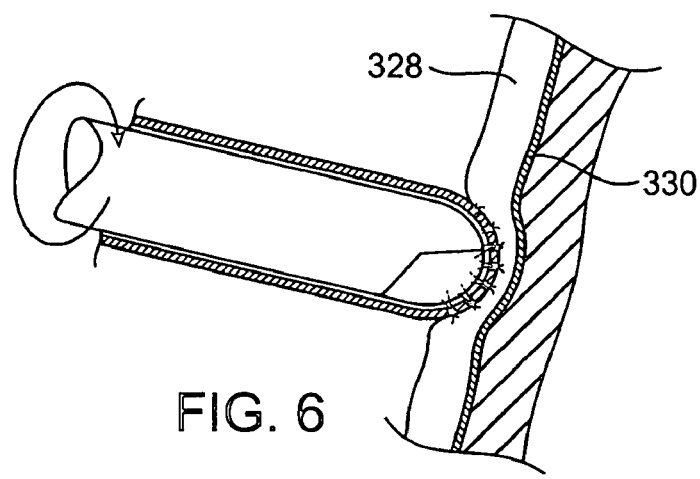
FIG. 6 illustrates an elevational distal end view of the device of FIG. 5.
Figure 5:
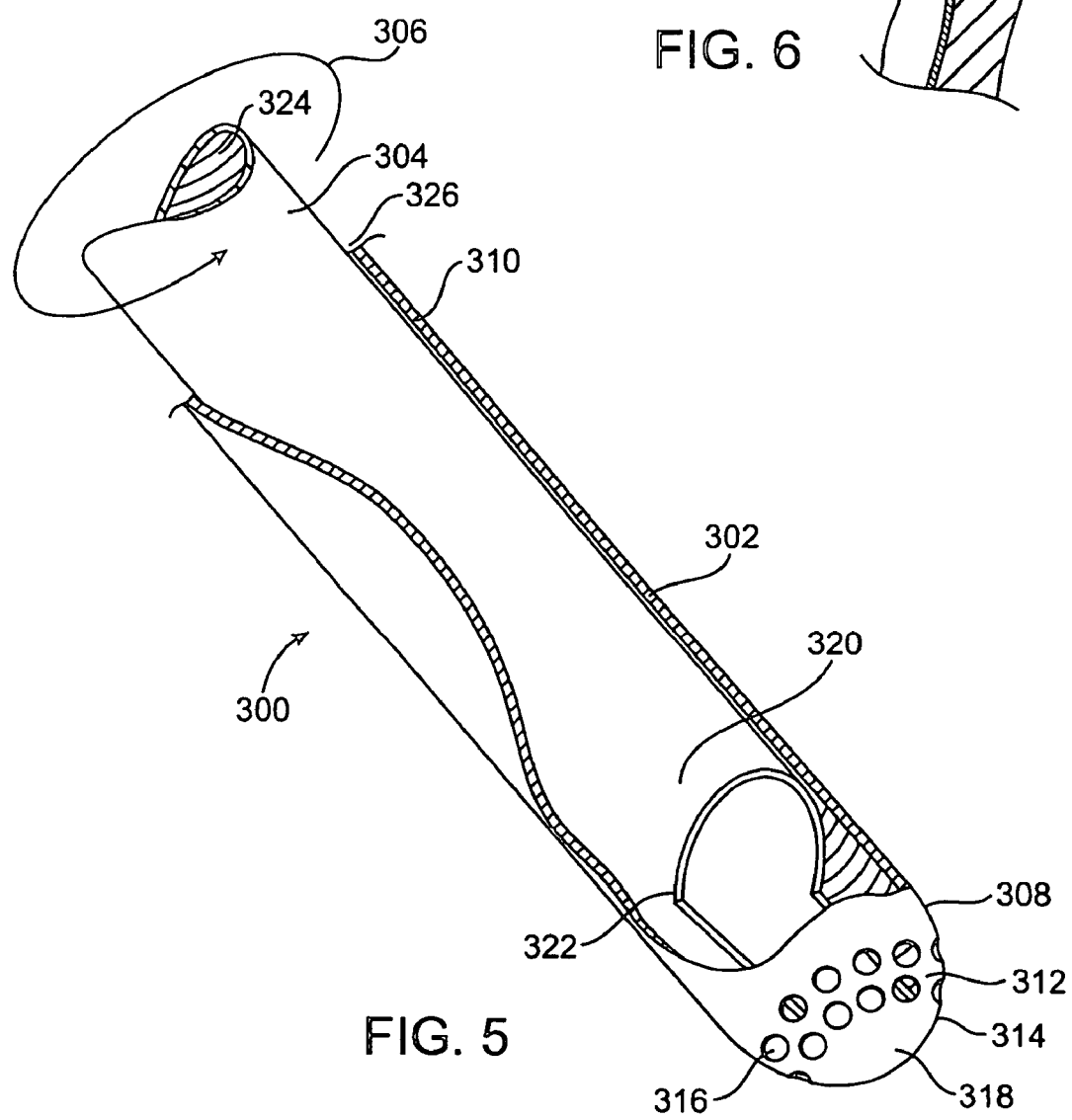
FIG. 5 illustrates a cross-sectional view of a third exemplary embodiment in accordance with the present invention, in use.
Figure 7:
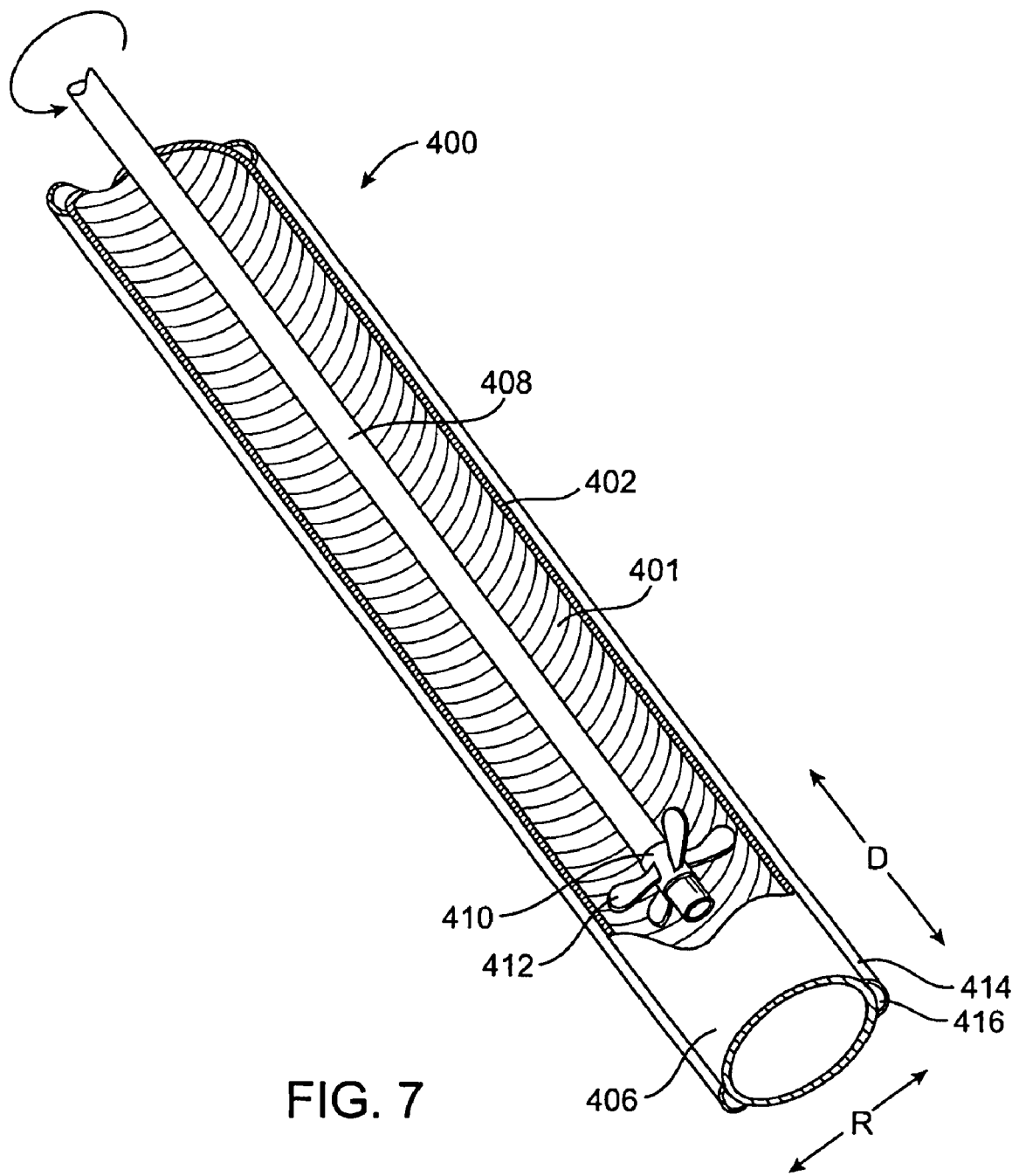
FIG. 7 illustrates a cross-sectional view of a fourth exemplary embodiment in accordance with the present invention, taken along line 7-7 in FIG. 8.

FIGS. 5 and 6 schematically illustrate views of a third exemplary embodiment of a fat removal device 300 in accordance with the present invention. Device 300 includes an outer cannula 302 having a longitudinally extending lumen 310 therein, and an inner cannula 304 mounted to rotate in the outer cannula's lumen, as indicated by arrow 306. Outer cannula 302 includes a distal end 308 which has a barrier 312 including at least one, and preferably a mesh or array of holes 316 which partially covers the open distal end of the outer cannula 302. As will be described in greater detail below, barrier 312 is provided to allow fatty tissue cells to extrude through the mesh or holes 316 in the barrier, while excluding nerves and blood vessels having a certain size, which underlie the fatty tissue layer, from passing through the barrier and into the lumen 310. Barrier 312 may take any of a number of configurations.

For example, barrier 312 can be a mesh or array of holes 316, a screen, a porous or slotted plate, hemisphere, dome, frustocone, or other geometry which functions to allow fatty tissue cells to extrude through the barrier when the barrier is pressed against fatty tissue, while excluding nerves and blood vessels having a certain size from passage through the barrier. In the exemplary embodiment illustrated in FIGS. 5 and 6, barrier 312 includes a dome or hemispherical member 314 which is joined to or integral with the distal end 308 of outer cannula 302. Member 314 includes an array of holes or passages 316 which are sized to allow fatty tissue to pass therethrough, but a small enough that certain sizes of nerves and blood vessels will not pass through the dome member.

For example, in optional preferred aspects, the passages 316 are dimensioned to be small enough such that nerve damage is avoided. For example, passages 316 may optionally be a diameter from 10% less than the diameter of the nerve to be protected to 6 mm. For example, and not by way of limitation, passages 316 have a diameter between 10% less than the diameter of the nerve to be protected and about 0.300 inches, preferably about 10% less than the diameter of the nerve to be protected. The spacing between the holes, from the centerline of one hole to the centerline of an adjacent hole, has been found by the inventors herein to be advantageously from the diameter of the nerve to be protected to 6 mm. The depth of passages 316, which corresponds in this embodiment to the thickness of member 314, is between about 0.015 inches and about 0.050 inches, preferably about 0.030 inches.] Barrier 314 can be made of any number of suitable materials which are biocompatible, of moderate to high strength, and are readily manufactured to the required specifications. For example, barrier 314 can be formed of plastics, including thermoplastic and thermoset materials, metals, including stainless steel and Nitinol, or ceramics.

As illustrated in FIG. 6, barrier 314 may optionally include a central portion 318 which does not include any passages 316 therethrough. Central portion 318 is provided as a bearing surface for the device 300 when it is pressed against and into fatty tissue, so that any nerves and larger blood vessels which may underlie the fatty tissue layer will not be in direct contact with passages 316, thus further ensuring that such nerves and larger blood vessels will not enter the passages.

Inner cannula 304 includes an elongated shaft which extends to a distal end 320. Distal end 320 has a shape which is complimentary to and extends into barrier 312. In the embodiment illustrated in FIGS. 5 and 6, the distal end 320 of the inner cannula is dome or hemispherical shaped. Distal end 320 also includes a blade, shearing member, scraper, or the like, designated 322 in FIG. 5. In the embodiment illustrated in FIG. 5, blade 322 is formed in the distal end 320 by the removal of a portion of the surface of the distal end of the inner cannula 304, leaving a portion of the surface the edges of which act as the blade 322. For example, ⅓ (120 degrees) of the distal end of the inner cannula can be removed to form blade 322. Thus, upon rotation of the inner cannula within the outer cannula, blade 322 rotates adjacent to the inner surface of barrier 316, and cuts, shears, and/or scrapes any material from the inner surface of the barrier which extends into the space swept out by the blade.

Inner cannula further includes a longitudinally extending lumen 324 which fluidly communicates the open portions of the distal end 322 with the proximal end of the inner cannula (not illustrated). Lumen 324 is preferably connected to a source of vacuum so that lumen 324 acts as an aspiration lumen. If desired, lumen 310 can be connected to a source of irrigation fluid, which fluid would then flow in the annular gap 326 between the inner and outer cannulae toward the distal end of the device 300.

Device 300 alternatively can incorporate a heating devices to heat the fatty tissue cells to aid in extruding them through barrier 312, and to cauterize the capillary bed which vascularizes the fatty tissue. For example, barrier 312 can include or itself be a heater which is selectively operable to slightly raise the temperature of the fatty tissue layer. Alternatively, irrigation fluid supplied through lumen 310 can be heated to provide a similar effect. To cauterize the fatty tissue capillary bed, preferably blade 322 is formed as an electrocautery tool, and is in electrical communication with an appropriate source of electrical power (not illustrated).

The function of device 300 will now be described with reference to FIGS. 5 and 6. The outer surface of the fatty tissue is made accessible to device 300, as described above. Barrier 312 is pressed up against fatty tissue 328, while, if provided, the tissue is heated by a heater in proximity to the fat. Inner cannula 304 is rotated, causing blade 322 to sweep past the inner openings of passages 316. As fat is extruded through passages 316 by application of pressure by barrier 312, it is cut or wiped away from the inner surface of the barrier, and simultaneously the capillary bed of the fatty tissue is cauterized by blade 322. Irrigation fluid can be continuously or selectively supplied through lumen 310, while aspiration through lumen 324 carries the irrigation fluid and fat away from the distal end of device 300. Nerves and myocardial tissue or a larger blood vessel 330 is effectively protected from the action of blade 322 because the size of passages 316 and the presence of central portion prevents the tissue or vessel from entering into the passages.

FIGS. 7-10 schematically illustrate views of a fourth exemplary embodiment of a fat removal and nerve protection device 400 in accordance with the present invention. As illustrated in cross-section in FIG. 7, as taken along line 7-7 in FIG. 8, device 400 includes a cannula 402 having a lumen 404 longitudinally extending from a distal end 406 toward a proximal end (not illustrated). A rotatable shaft 408 extends through lumen 404 toward distal end 406, terminating at a rotary cutting element 410 having at least one, and preferably a plurality of, cutting blades 412. Blades 412 are alternatively also formed as electrocautery tools, as described above in the preceding embodiments, for cauterizing the capillary bed in the fatty tissue cut by device 400. In an alternative embodiment (not illustrated), blades 412 are shaped as an auger, paddle, propeller, or fan blade, such that the leading edge of each blade as it rotates is ahead of the trailing edge of each blade, which will cause any tissue and fluid impinged upon by each of the blades to be pushed proximally. The distalmost extent of blades 412 is located a distance D from the distalmost end of cannula 402. Cannula 402 has an outer diameter at its distal end of R.

Figure 8:
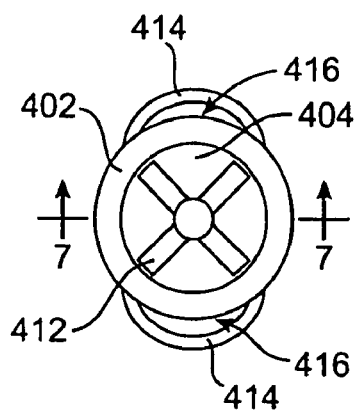
FIG. 8 illustrates an elevational distal end view of the device of FIG. 7.

As illustrated in the end view of FIG. 8, device 400 is further provided with at least one, and preferably a plurality of, external fluid flow conduits 414, each defining a fluid flow lumen 416. Lumina 416 can be formed alone by each of the conduits 414, or, as illustrated in FIG. 8, can be formed between the outer surface of cannula 402 and the inner surface of each of conduits, in order to reduce the cross-sectional profile of device 400 without compromising the cross-sectional area of each of the lumina. Conduits 414 are preferably irrigation conduits, and are preferably in fluid communication with a source of irrigation fluid at their proximal ends (not illustrated). As discussed above, the irrigation fluid is preferably heated and either continuously or selectively delivered through conduits 414.

Figure 9:
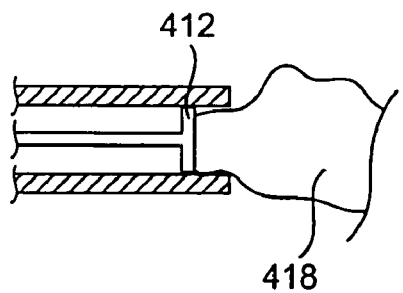
FIGS. 9 and 10 illustrate the device of FIG. 7, in use.
Figure 10:
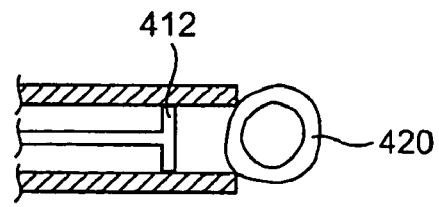

As with the preceding embodiments, device 400 is constructed to allow fatty tissue to enter into cannula 402, but prevents nerves, larger blood vessels and organ tissue from being impinged upon and cut by blades 412. In the embodiment illustrated in FIGS. 7-10, this is accomplished by selecting the distances D and R and their ratio (D/R) to preclude entry of these structures from being cut by blades 412. By way of example and not by limitation, in one embodiment of device 400, D is a distance from 10% less than the diameter of the nerve to be protected to 6 mm, R is a diameter from 10% less than the diameter of the nerve to be protected to 6 mm), and D/R is about 1.0. Thus, as illustrated in FIGS. 9 and 10, compliant materials such as fatty tissue 418 can extrude into lumen 404 to be cut and cauterized by blades 412 (FIG. 9), while less compliant materials such an organ tissue and larger blood vessels 420 cannot extend into the lumen to be cut by the blades. Furthermore, the orientation of the apertures may be such that the nerves which run in one direction are not parallel to the aperture's long axis.

The function of device 400 will now be described with reference to FIGS. 7-10. In a manner similar to devices 100, 200, and 300, device 400 is pressed against fatty tissue 418 to extrude the tissue into lumen 404. Rotating blades 412 cut, and preferably simultaneously cauterize, the tissue and its capillary bed, while irrigation fluid is supplied though conduits 414 to the surgical site. Cut tissue and fluid is aspirated through lumen 404, aided by the action of blades 412 pushing the tissue and fluid proximally. Larger blood vessels 420, nerves and organ tissues are precluded from entering into lumen 404 far enough to be cut by blades 412.

Figure 11:
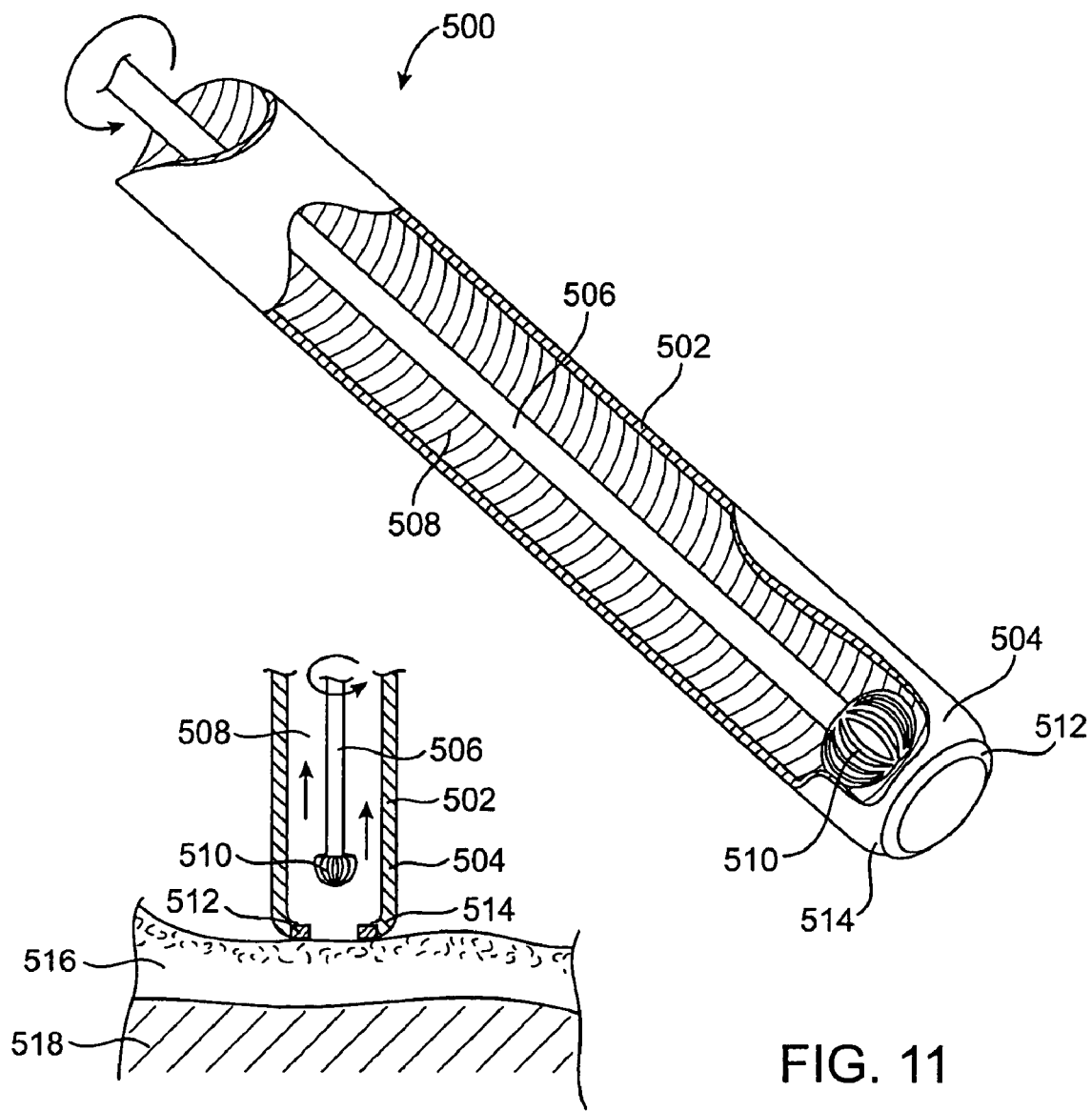
FIG. 11 illustrates a cross-sectional view of a fifth exemplary embodiment in accordance with the present invention, in use.
Figure 12:
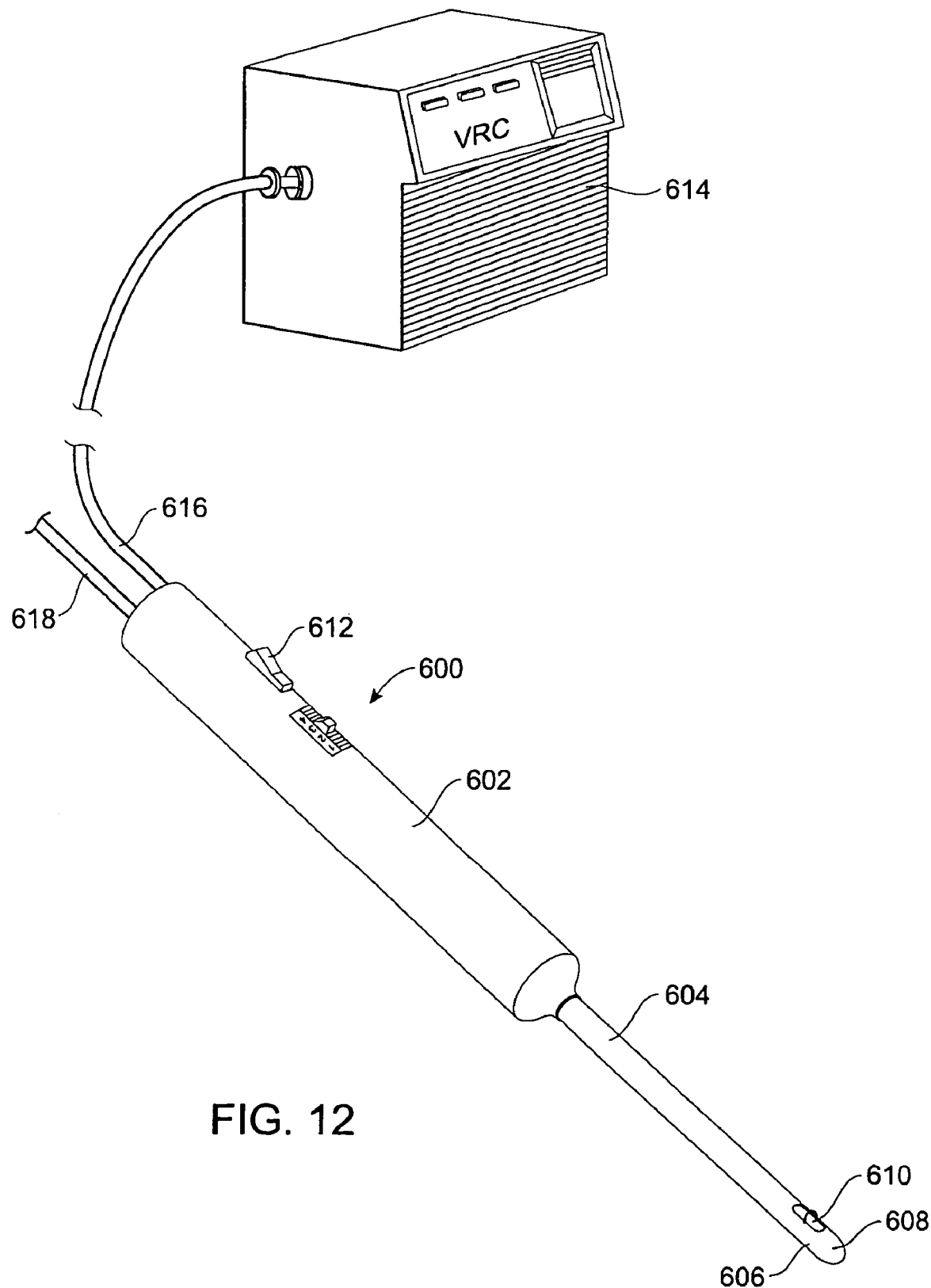
FIG. 12 schematically illustrates a view of a sixth exemplary embodiment in accordance with the present invention.

FIG. 11 schematically illustrates a view of a fifth exemplary embodiment of a fat removal and nerve protection device 500 in accordance with the present invention. Device 500 is similar to device 400 in some respects. Device 500 includes a cannula 502 extending from a distal end 502 toward a proximal end 504 (not illustrated). A rotatable shaft 506 is located in a longitudinally extending lumen 508. Shaft 506 carries a cutting head 510 which is recessed in lumen 508 from the distal end 502, and is optionally also constructed as an electrocautery tool. Distal end 502 preferably is provided with heaters 512 at the distalmost end of cannula 502, for heating fatty tissue 516 against which the cannula is pressed. Heaters 512 can be any suitable heater, including RF and DC heaters. Lumen 508 is preferably in fluid communication with a source of suction (not illustrated) so that lumen 508 will act as an aspiration lumen. The tip 514 is preferably directed radially inwardly, to preclude nerves, larger blood vessels and organ tissue 518 from entering into lumen 508, similar to the function of the dimensions D and R of the distalmost end of device 400. Irrigation conduits (not illustrated) may optionally be provided on the exterior of cannula 502, similar to conduits 414.

The function of device 500 will now be described with reference to FIG. 11. In a manner similar to devices 100, 200, 300, and 400, device 500 is pressed against fatty tissue 516 to extrude the tissue into lumen 508. Rotating blade 510 cuts, and preferably simultaneously cauterizes, the tissue and its capillary bed, while irrigation fluid is optionally supplied to the surgical site. Cut tissue and fluid is aspirated through lumen 508. Nerves, larger blood vessels and organ tissues 518 are precluded from entering into lumen 508 far enough to be cut by blade 510.

FIGS. 12-16 schematically illustrate views of a sixth exemplary embodiment of a fat removal and nerve protection device 600 in accordance with the present invention. Device 600 includes a handle 602 shaped to be easily grasped by a practitioner's hand, and a cannula 604 extending distally from the handle toward a distal end 606. Distal end 606 is closed off, as at 608, and includes a vacuum port or opening 610 which is sized and constructed allow fatty tissue to enter into the opening, which preventing nerves, larger blood vessels and organ tissue from entering.

A vacuum source 614 is in fluid communication with opening 610 though aspiration conduit 616 and handle 602, as will be described in greater detail below. Handle 602 further includes a switch or lever 612 for selectively operating device 600, and is connected to a source of power (not illustrated) via conduit 618.

Figure 13:
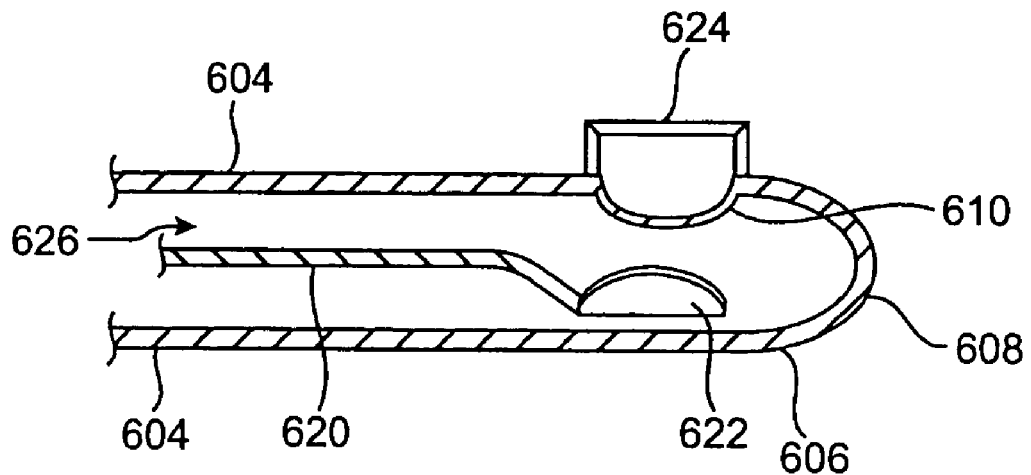
FIG. 13 illustrates a cross-sectional view of distal portions of the device of FIG. 12.
Figure 14:
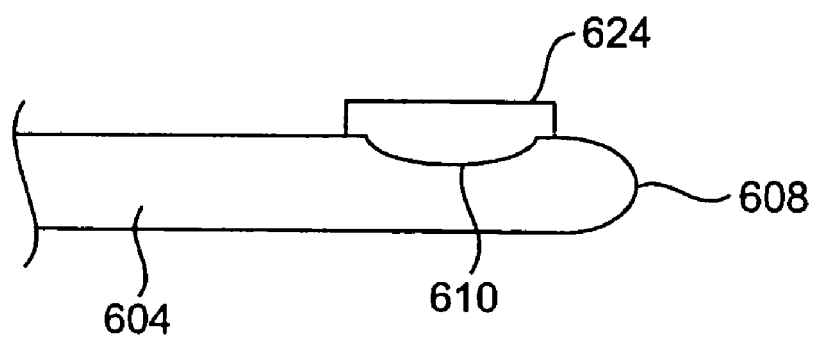
FIG. 14 illustrates an elevational side view of the device of FIG. 12.

FIG. 13 illustrates a cross-sectional view of the distal tip 606 of the fat removal and nerve protection device 600. Tip 606 is preferably constructed out of a hollow tube, such as a hypotube made of stainless steel, Nitinol, or a rigid polymer, has a blunt distal end 608 to prevent damaging tissue with the end of the probe, and includes a fluid lumen 626. On the side of the tube is a vacuum port 610 to allow fat to be sucked into the cannula. A centrally located rotatable knife blade shaft 620 is provided within the cannular. Attached to the distal end of the shaft 620 is a semicircular knife blade 622 that rotates along the inner surface of the tube to cut the fat that has been sucked into the cannula.

Figure 15:
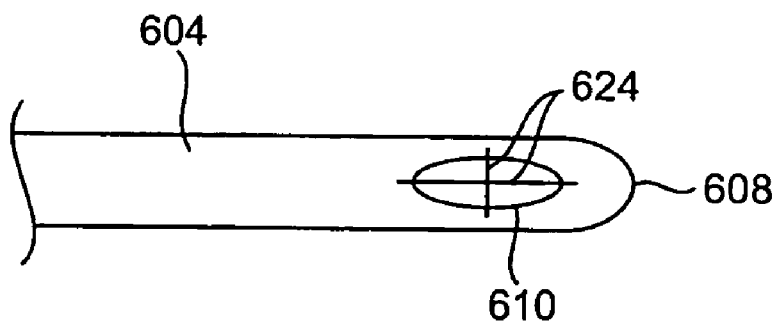
FIG. 15 illustrates a top plan view of the device of FIG. 12.

Optionally, an artery/vein guard 624 is attached to the outer surface of the cannula that keeps nerves and medium sized arteries out of the port. In the embodiment illustrated in FIGS. 12-16, guard 624 is a piece of thin protective material that projects from the outer surface of the cannula a short distance and then traverses the port opening. FIG. 15 illustrates an alternate configuration for guard 624, where the guard has a cross-hair configuration to prevent damage to the nerves or blood vessels, e.g., coronary arteries or veins, when device 600 is used at different angles to the organ, e.g., heart. Other types of guards could also be used within the spirit and scope of the invention, such as posts located around the port opening, and/or a wide mesh around the port opening, as described above with reference to devices 100 and 300. By way of example and not by limitation, the largest spacings between the portions of guard 624 which traverse port 610 are preferably between 10% less than the diameter of the nerve to be protected to 6 mm.

Knife blade 622 is preferably formed in an arc, so that the fatty tissue which enters into port 610 is sheared and carried into lumen 626. Optionally, the knife blade is connected to a source of electric energy (not illustrated) such that the blade can cauterize while it cuts the fat. The knife blade may also be constructed as a unipolar cauterizer, in which case a grounding pad (not illustrated) would be connected to the patient in a location remote from the blade. The knife blade can also be constructed as a bipolar cauterizer, in which case the knife blade would be one pole, and distal tip 606 would be another pole. If a bipolar configuration is utilized, the distal tip 606 is preferably insulated from the rest of the cannula, by being formed separately with an insulating segment between the distal tip and the remainder of the cannula, and the inner surface of the cannula would have to be insulated from the rotating knife blade 622, for example by coating with an appropriate dielectric material, e.g., PTFE.

Figure 16:
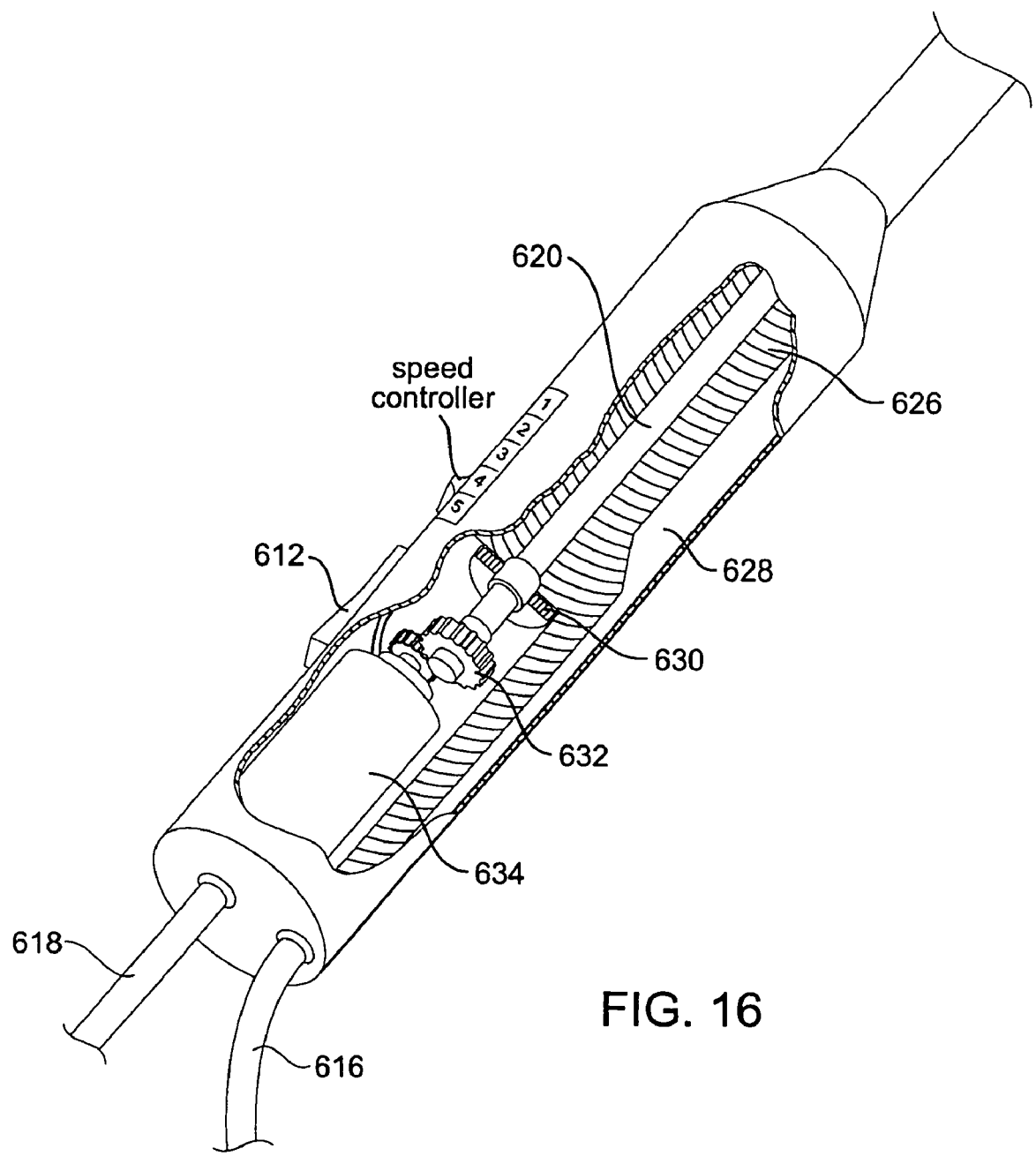
FIG. 16 illustrates a cross-sectional view of proximal portions of the device of FIG. 12.
Figure 17:
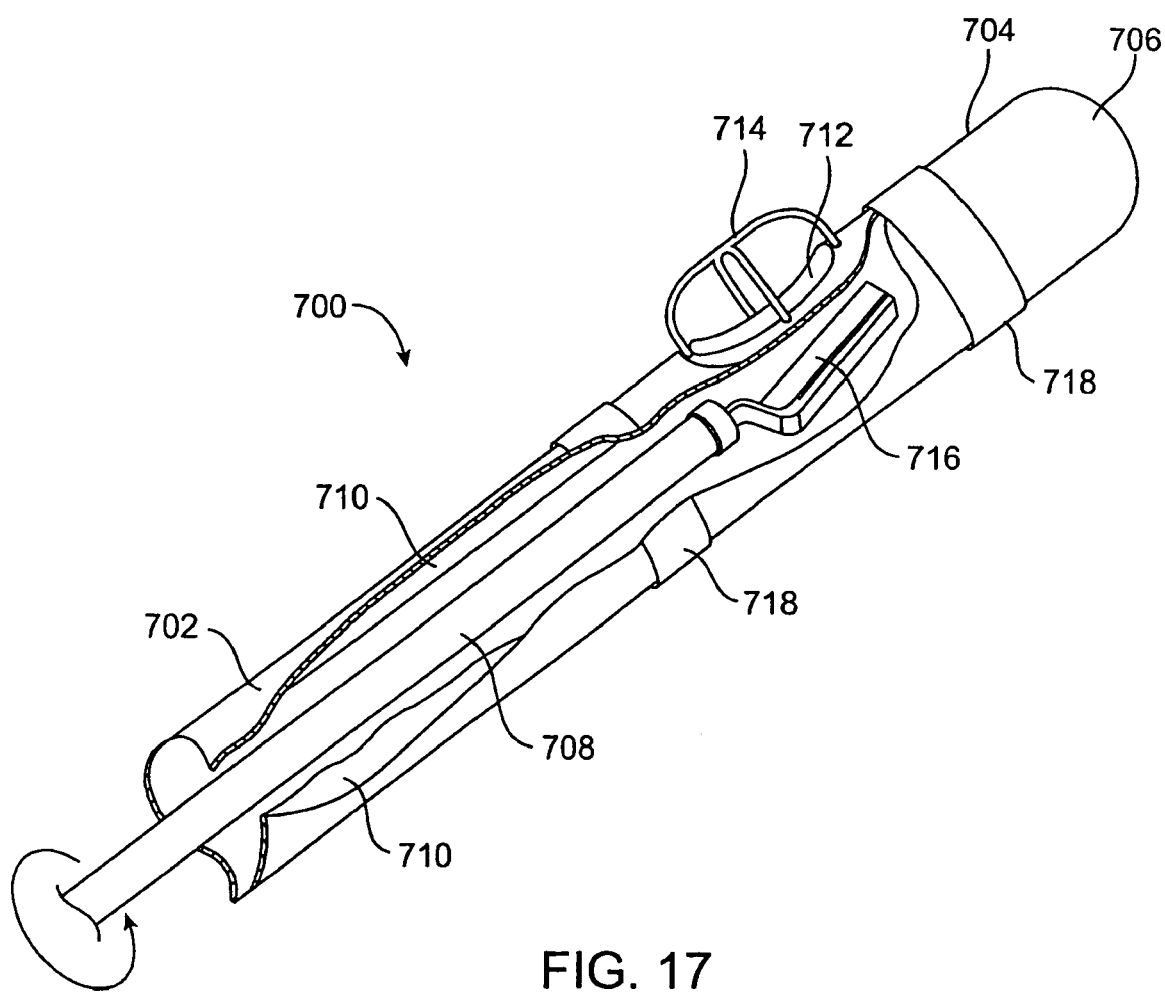
FIG. 17 illustrates a cross-sectional view of distal portions of a seventh exemplary embodiment in accordance with the present invention.

Turning now to FIG. 16, handle 602 of the fat removal and nerve protection device is schematically illustrated. Handle 602 is provided with a means for turning the remover on and off 612, such as an on/off lever. Means 612 is operatively connected to the sources of power and vacuum to turn them on and off. A connection 628 is made between the vacuum tubing 616 and lumen 626. A seal 630, e.g., an O-ring, is placed around the knife blade shaft 620 to ensure that the vacuum is not lost proximal of the port opening 610 in the distal tip 606. At the proximal end of the knife blade shaft 620, a gear 632 is provided which attaches the shaft 620 to a motor assembly 634. Motor 634 could be an electric motor, a pneumatic motor, as are commonly found in dental drills, or any other standard type of motor. The power source (not illustrated) to which motor 634 is connected is a source of power appropriate for powering motor 634, e.g., a source of DC power, AC power, high pressure air, or high vacuum. The knife 622 can be operated at any desired speed (revolutions per minute), either a fixed or selectively variable as will be readily apparent to one of ordinary skill in the art.

There are numerous modifications that can be made to device 600 without departing from the inventive concept herein. For instance, rotating knife blade 622 could be attached via a rotating tube (not illustrated) instead of shaft 620 (or shaft 620 could be made to include a longitudinally extending lumen), and the aspiration lumen would always be in the center of the cannula and the rotating tube. Furthermore, the amount of vacuum supplied can vary to optimize sucking of the fat. Port 610 and guard 624 can optionally be provided at the distalmost end of device 600.

The function of device 600 will now be described with reference to FIGS. 12-16. Device 600 is preferably used by a health care practitioner by incising the pericardium connective tissue layer and inserting tip 608 of the device into an area of fat to be removed. On/off lever 612 is depressed, vacuum applied, and knife 622 would begin rotating. Optionally, if provided, power is supplied to blade 622 so that it acts as a cauterizer. The practitioner would then carefully remove the fat from the pericardium and over the myocardium while leaving the coronary vessels intact, but pressing the distal tip 606 of device 600 against the fatty tissue, which will extrude through guard 624, and be cut by the blade. The use of the vessel protectors should allow the practitioner to be able to remove fat from close to the coronary blood vessels without damaging them or nerves on or near the pericardium adjacent thereto, because the coronary vessels would not enter into port 610 because of guard 624.

Once the fat is removed from an area of the heart, the practitioner can then inspect the area and determine if there is any bleeding from the small vessels that were connecting the fat tissue. These could then be cauterized using a standard electrocautery tool, if device 600 either is not provided with an electrocautery function, or if the electrocautery was incomplete. If the knife blade also served as an electrocauterizer, then there should be very limited bleeding and oozing from the fat removal.

FIGS. 17-20 schematically illustrate views of portions of a seventh exemplary embodiment of a fat removal and nerve protection device 700 in accordance with the present invention. Device 700 is a modification of device 600; accordingly, only those features of device 700 which differ from corresponding features of device 600 will be described. Device 700 includes a longitudinally extending cannula 702 which terminates at a distal end 704 in a closed blunt tip 706. A longitudinally extended rotatable shaft 708 extends through a lumen 710 of cannula 702. An aspiration port 712 fluidly communicates lumen 710 with the exterior of cannula 702. An artery/vein guard 714 extends out from around port 712 in a manner similar to artery/vein guard 624, described above.

Blade 716 is attached or otherwise formed at the distal end of shaft 708 immediately adjacent to port 712. Blade 716 is similar, but not identical to, blade 622. Blade 716 is shaped with a profile which is similar to an auger or the like, to push the material which extrudes through port 712 in a proximal direction when the blade rotates. Different from an auger, however, blade 716 still has a curved profile when viewed from the distal end thereof, and tapers proximally down toward shaft 708. Additionally, device 700 is provided with a bipolar electrocautery element, which in the embodiment illustrated in FIGS. 17-20 includes blade 716. Blade 716 forms one pole of the bipolar electrocautery element, while device 700 is further provided with ring electrodes 718 which extend around cannula 702 on the proximal and distal sides of port 712. Thus, blade 716 is one pole, while ring electrodes 718 are the other pole, of the bipolar electrocautery element. Suitable electrical leads for ring electrodes 718 are provided to provide a voltage at the ring electrodes (not illustrated), which leads can be located inside lumen 710 and through the wall of cannula 702, can be located on the exterior surface of the cannula, or can be embedded in the cannula wall itself. The details of bipolar electrocautery are well known by one of ordinary skill in the art, and are therefore not described herein.

Figure 18:
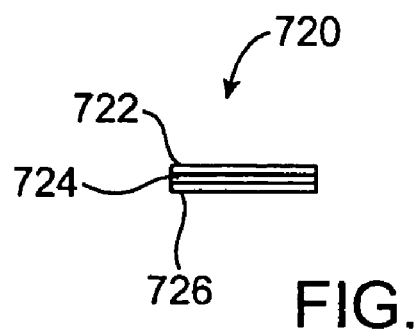
FIG. 18 illustrates an elevational side view of an alternate embodiment of portions of the device of FIG. 17.
Figure 19:
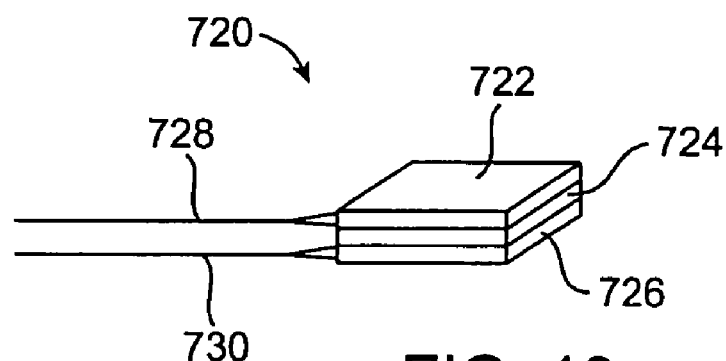
FIG. 19 illustrates a perspective view of the device of FIG. 18.
Figure 20:
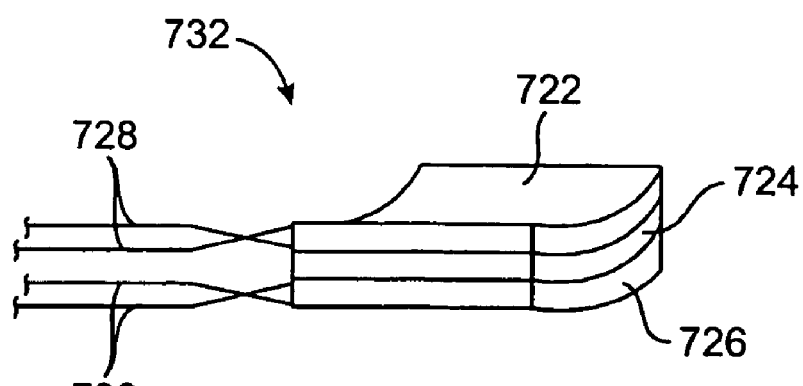
FIG. 20 illustrates a perspective view of another alternate embodiment of portions of the device of FIG. 17.

FIGS. 18-20 illustrate an alternative embodiment of blade 718, which itself is a bipolar electrocautery device. Blade 720, an end view of which is illustrated in FIG. 18, includes at least three layers: a top conductive layer 722, which forms one pole of the bipolar electrocauterizer; a middle insulating layer 724; and a bottom layer 726, which forms a second pole of the bipolar electrocauterizer. FIG. 19 illustrates a perspective view of blade 720, and further illustrates electrical conductors 728 and 730 leading to top layer 722 and bottom layer 726, respectively. Conductors 728, 730 may be carried by shaft 708, or may be formed integral therewith. Suitable electrical insulation is provided around conductors 728, 730, as will be readily apparent to one of ordinary skill in the art. FIG. 20 illustrates yet another embodiment of the blade for device 700, in which blade 732 is curved in a manner similar to blade 622, described above.

The function of device 700 is the same as for device 600, except that the bipolar electrocautery element of device 700, and specifically blade 716, cauterizes the capillary bed of the fatty tissue which is cut by the blade.

Figure 21:
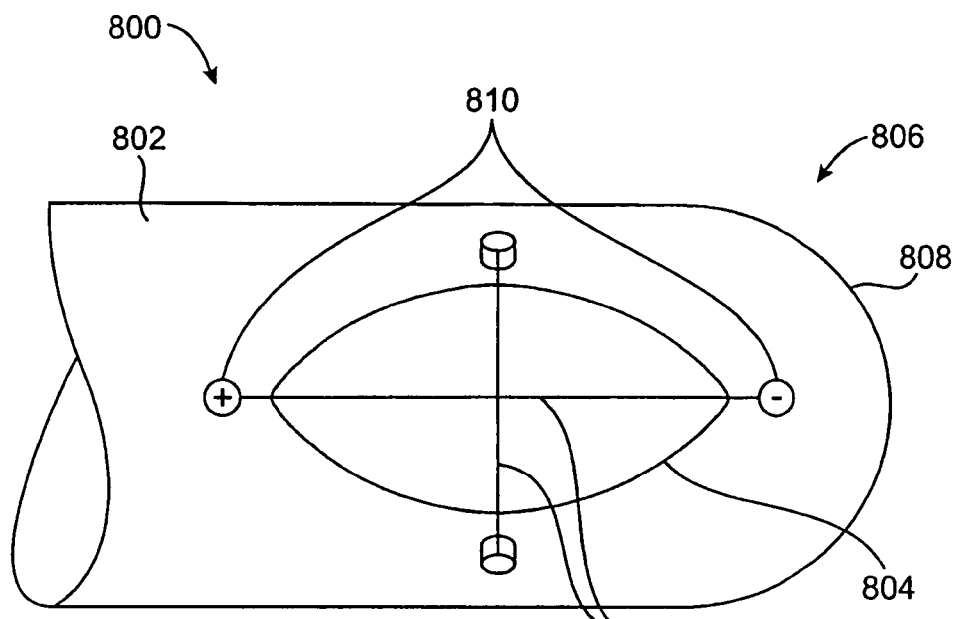
FIG. 21 illustrates a top plan view of a eighth exemplary embodiment in accordance with the present invention.
Figure 22:
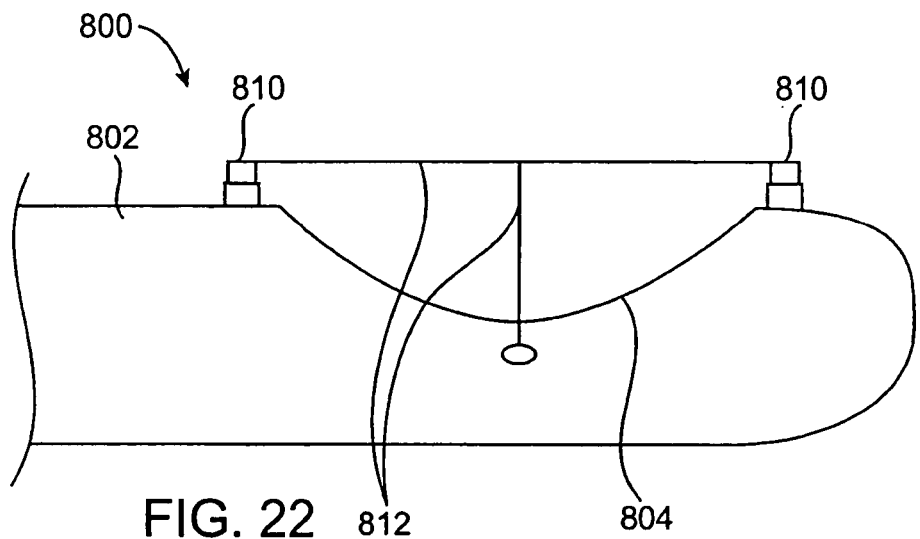
FIG. 22 illustrates an elevational side view of distal portions of the device of FIG. 21.
Figure 23:
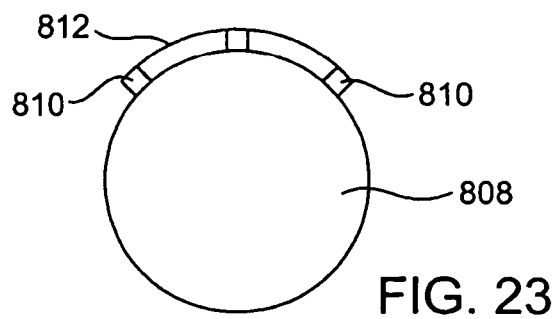
FIG. 23 illustrates an elevational end view of distal portions of the device of FIG. 21.

FIGS. 21-23 schematically illustrate views of portions of an eighth exemplary embodiment of a fat removal and nerve protection device 800 in accordance with the present invention. Device 800 is similar to devices 600 and 700, except that the fat is heated using RF monopolar or bipolar electrodes that protrude from the outer surface of the distal end of the device to heat, melt, and/or soften the fat to make it easier for the fat to be sucked into the vacuum port opening.

Turning now to FIGS. 21-23, device 800 includes a cannula 802 having a distal end 806 terminating in a blunt tip 808. A nerve/artery/vein guard 812 is positioned over a vacuum port opening 804 in the distal end 806 to prevent blood vessel, e.g., a coronary artery/vein, from being sucked into the fat removing device 800. Nerve/artery/vein guards 812 do not conduct electric energy and are attached to electrode posts 810 protruding from the outer surface of the cannula adjacent to port opening 804. Electrodes 810 are used to deliver RF energy to the fat tissue to heat the tissue to help make the tissue easier to be sucked into the tube. Electrodes 810 can be operated to heat the fatty tissue over a range of temperatures. Preferably, electrodes 810 heat the adjacent fat to a temperature between about 37 degrees centigrade and about 45 degrees centigrade, which the non-fatty tissues should tolerate well. According to another embodiment, a thermocouple could be provided at the intersection of artery/vein guard members 812 to give temperature feedback to an RF controller. One suitable controller is a Stellartech RF generator, available from Stellartech Research Corporation, Mountain View, Calif.

The function of device 800 is the same as for device 700, except that RF electrodes 810 of device 800, heats the fatty tissue which is cut by the blade (not illustrated).

Figure 24:
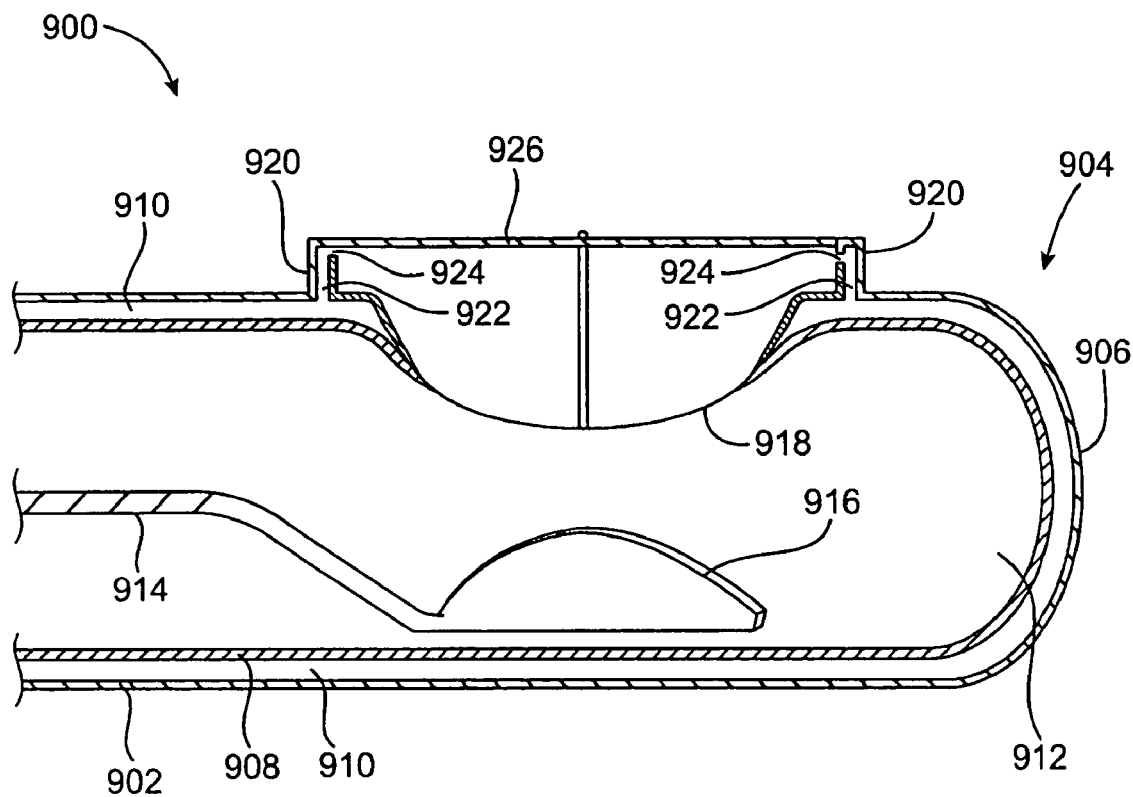
FIG. 24 illustrates a cross-sectional view of distal portions of a ninth exemplary embodiment in accordance with the present invention.
Figure 25:
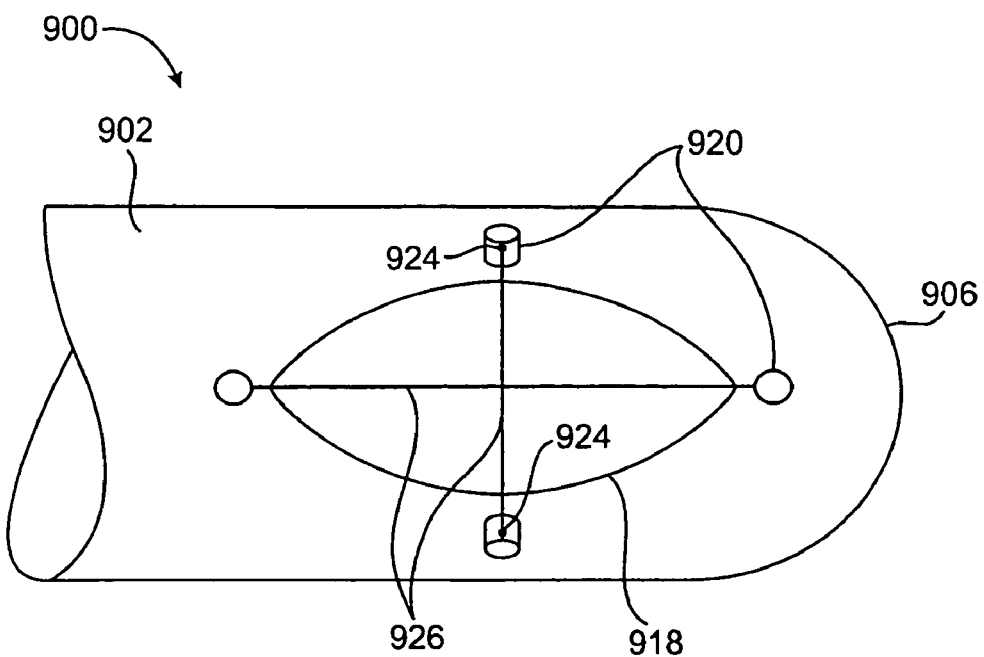
FIG. 25 illustrates a top plan view of the portions of the device in FIG. 24.
Figure 26:
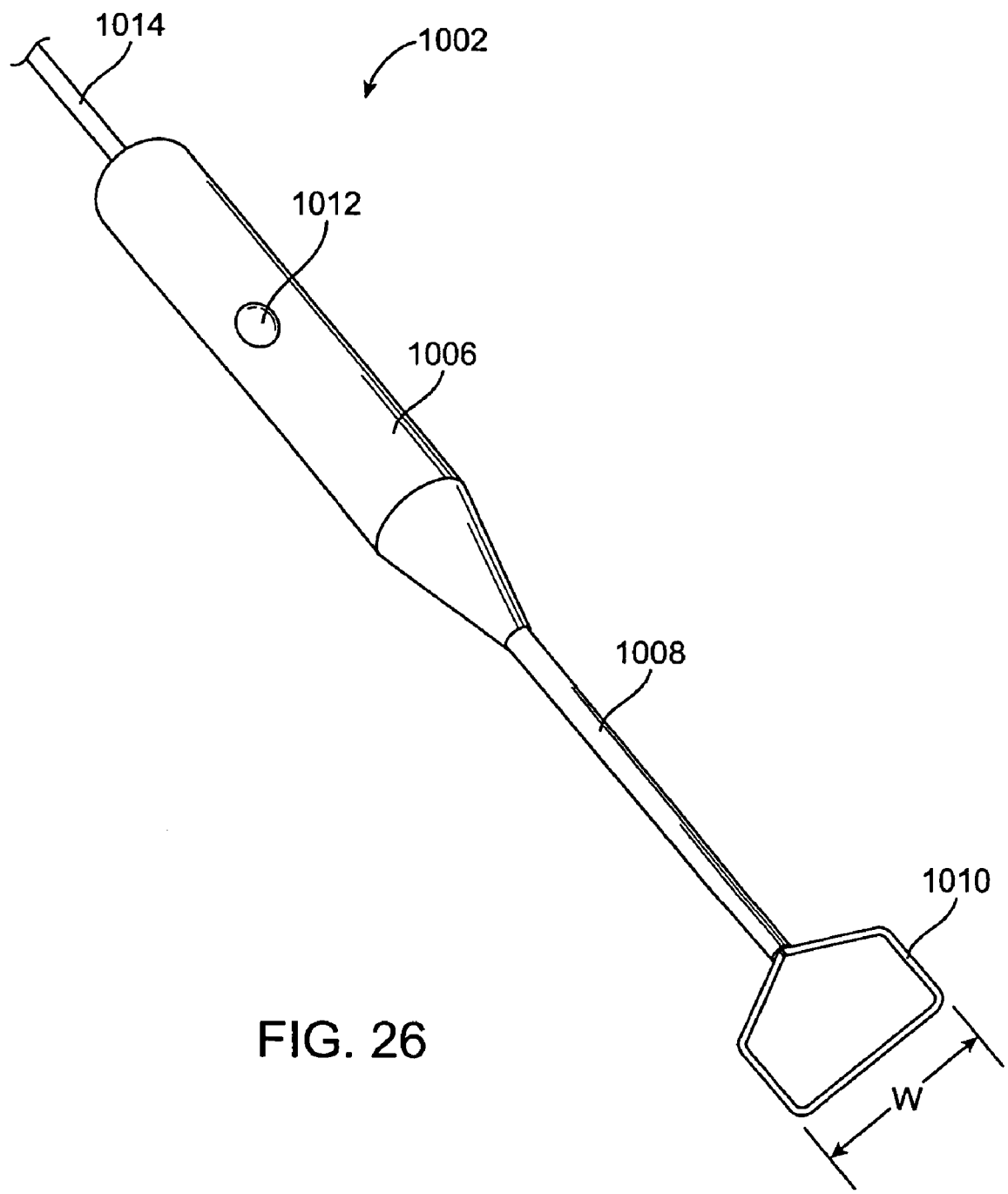
FIG. 26 illustrates a perspective view of portions of a tenth exemplary embodiment in accordance with the present invention.

FIGS. 24 and 25 schematically illustrate views of portions of a ninth exemplary embodiment of a fat removal and nerve protection device 900 in accordance with the present invention. Device 900 is similar to the devices 600, 700, and 800, with the addition of structures for spraying pressurized liquid from at least one spray nozzle to assist in cutting the fatty tissue.

Turning now to the drawing figures, FIG. 24 illustrates a cross-sectional view of distal portions of device 900, while FIG. 25 illustrates a top plan view of the distal end of the device. Device 900 includes an inner cannula 908 and an outer cannula 902, which form a fluid lumen 910 between them and which is in fluid communication with a source of pressurized fluid (not illustrated) at the proximal end of device 900. Inner cannula 908 has an inner fluid lumen 912, which is preferably in fluid communication with a source of suction. Distal end 904 of device 900 includes a blunt tip 906, similar to the blunt tips of devices 600, 700, and 800.

A rotatable shaft 914 extends through lumen 912 and carries rotatable blade 916 at distal portions thereof immediately adjacent aspiration port 918. Blade 916 can alternatively be constructed similar to blades 622, 716, 720, or 732, described above. Nerve/artery/vein guards 926 are also provided to prevent a blood vessel from entering into port 918. To assist in cutting fat which is adjacent to port 918, device 900 includes high pressure spray nozzles 924 carried on posts 920 which extend away from outer cannula 902 around port 918. Nozzles 924 are in fluid communication with lumen 910, which carries high pressure fluid, via connecting conduits 922 in posts 920. Nozzles 924 are directed inwardly, that is, toward the center of opening 918. Preferably, nerve/artery/vein guard 926 is carried by posts 920.

As described above, the high pressure liquid can be optionally heated for delivery to nozzles 924. Heating the liquid can help melt, soften, and/or dissolve the fat such that the fat is sucked into vacuum port 918 opening easier. The liquid can also lubricate the fat such that aspiration lumen 912 does not get clogged with fat.

Optionally, RF electrodes (not illustrated) could be further incorporated into device 900, to help heat, melt, and/or soften the fat. The RF electrodes are preferably placed on top of spray nozzles 920. A thermocouple (not illustrated) could also be included, preferably at the intersection of nerve/artery/vein guard 926.

There are numerous further modifications to device 900 that can be made without departing from the inventive concept herein. For example, the liquid could be pumped to spray nozzle(s) 922 instead of using a pressurized reservoir. Different liquid solutions could be used, such as ones including therapeutic agents, lipophilic agents to aid in dissolving the fat, or the like. The vacuum pressure can be increased to assist the removal of the fat. The knife blade can be made in different configurations, as described above. The knife blade can be connected to a rotating tube, as described above, instead of rotating shaft 914 and the vacuum lumen can be inside the rotating tube.

The function of device 900 is substantially the same as for device 800, except that pressurized fluid is sprayed out of nozzles 922 while blade 916 cuts tissue. Furthermore, the pressurized liquid can be heated, which in turn will heat the fat and help drive the fat into the vacuum port opening to be cut by the rotating knife blade. As described above, RF energy may also be used to help heat, melt, and/or soften the fat.

FIGS. 26-29 schematically illustrate views of portions of a tenth exemplary embodiment of a fat removal device 1000 in accordance with the present invention. Device 1000 includes an electrocautery wand 1002 (see FIG. 26) and a fat extrusion and nerve protection tool 1004 (see FIG. 27). Wand 1002 includes a handle portion 1006, from which an extension 1008 extends. An electrocautery loop 1010 extends from the distal end of extension 1008. Electrocautery loops per se are well known to one of ordinary skill in the art. Handle 1006 includes a control switch 1012 which functions to control the application of energy to loop 1010, thereby controlling the cauterizing function of the loop. A power cable 1014 extends from a proximal end of handle 1006.

Figure 27:
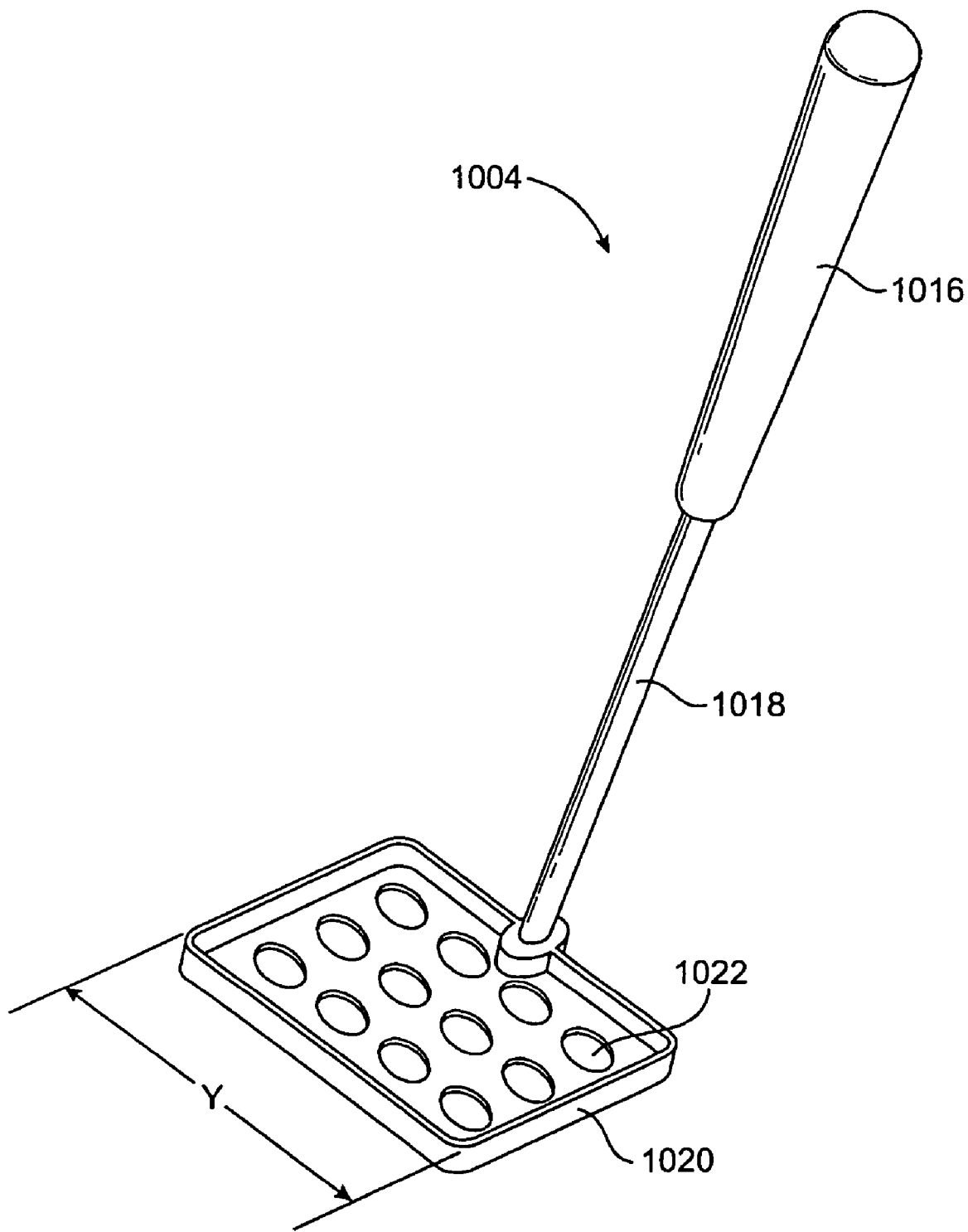
FIG. 27 illustrates a perspective view of other portions of the device of FIG. 26.
Figure 28:
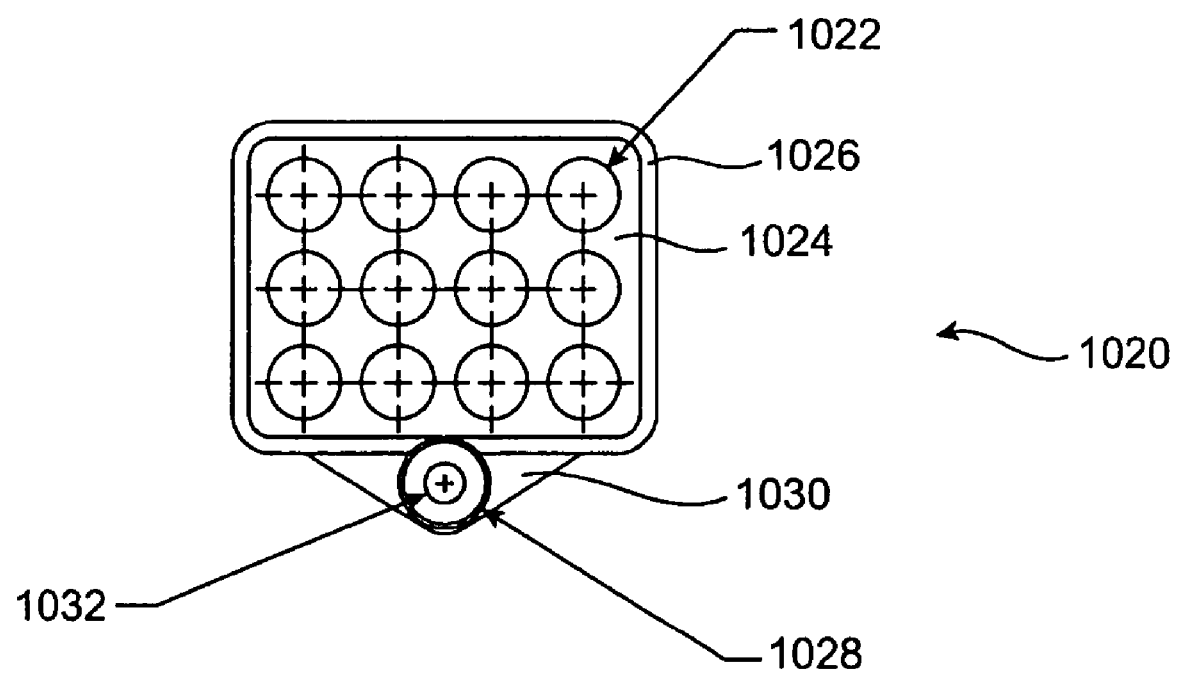
FIG. 28 schematically illustrates a top plan view of portions of the device in FIG. 27.
Figure 29:
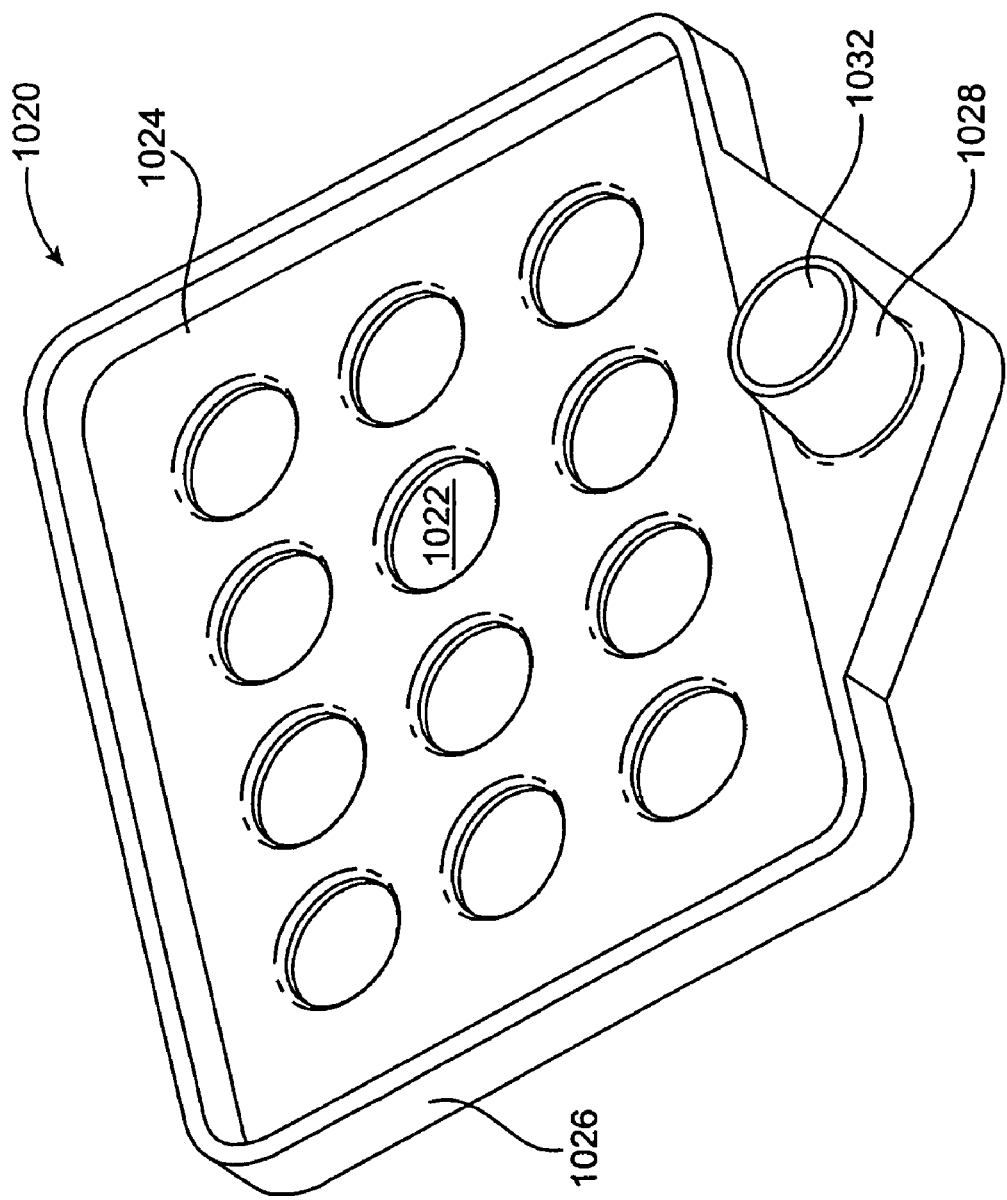
FIG. 29 illustrates a perspective view of the portions of FIG. 28.

Fat extrusion and nerve protection tool 1004 is constructed to be used in conjunction with wand 1002. Tool 1004 includes a handle 1016, an extension 1018, and a screen 1020 attached to the extension. Screen 1020 includes at least one, and preferably a plurality of holes or passages 1022 through which fat can be extruded, to be wiped away and cauterized by loop 1010 of wand 1002. As illustrated in the embodiment of FIGS. 27-29, passages 1022 are more preferably arranged in a regular array, although the passages can be arranged in irregular patterns, or even randomly, and still be within the spirit and scope of the present invention. Screen 1020 is specially sized constructed to be usable with wand 1002, as described in greater detail with reference to FIG. 28.

Turning now to FIG. 28, which is a schematic illustration of screen 1020, and FIG. 29, which is a perspective illustration of the screen, the screen has a generally rectangular configuration. Screen 1020 can also be formed in other geometric configurations, such as circles, ovals, slits, squares, triangles, and the like. Screen 1020 includes a plate 1024 through which passages 1022 are formed. An upstanding lip 1026 extends from plate 1024, and defines the working area of screen 1020. The width Y of plate 1024 between opposite sides of lip 1026 is selected to be approximately the same as, and preferably slightly greater than, width W of electrocautery loop 1010 (see FIG. 26). By selecting dimensions Y and W in this manner, lip 1026 also functions as a restrain on the range of motion of loop 1010, indicating to the practitioner that the loop is adjacent the edge of screen 1020. Thus, lip 1026 aids in preventing cauterization of tissue other than that which has been made to extrude through passages 1022 of screen 1020.

Screen 1020 further includes a flange 1030 attached to one side of plate 1024, which includes an upstanding post 1028. Post 1028 includes a central blind bore 1032. Post 1028 is provided as a means to attach handle 1016 and extension 1018 to screen 1020, for which extension 1018 is provided with a member (not illustrated) which mates with blind bore 1032 to join the extension to the screen. Flange 1030 distributes forces transmitted through handle 1016 and extension 1018 to screen 1020, as described below.

In a preferred embodiment of device 1000, passages 1022 have diameters between 10% less than the diameter of the nerve to be protected to 6 mm. The spacing between the passages is between about 0.005 inches and about 0.500 inches, preferably about 0.020 inches. The depth of passages 1022, which corresponds in this embodiment to the thickness of plate 1024, is between about 0.015 inches and about 0.050 inches, preferably about 0.030 inches. Screen 1020 can be made of any number of suitable materials which are biocompatible, of moderate to high strength, and are readily manufactured to the required specifications. For example, screen 1020 can be formed of plastics, including thermoplastic and thermoset materials, metals, including stainless steel and Nitinol, or ceramics.

The function of device 1000 will now be described with reference to FIGS. 26-29. An organ which has a fatty tissue layer is exposed by, e.g., thorachotomy. A practitioner grasps wand 1002 and tool 1004 in each hand, and presses tool 1004 against the surface of the fat. Fat is thereby caused to extrude through the passages 1022. The practitioner then presses control switch 1012, and wipes electrocautery loop 1010 across that portion of plate 1024 inside lip 1026 to simultaneously scrape the fat away and cauterize the capillary bed in the fatty tissue. If desired, loop 1010 may be used without application of energy to the loop, and control switch 1012 may be selectively operated to cauterize only some of the time. When a sufficient amount of fat has been wiped away from a particular site, the screen is moved to another location on the organ, e.g., heart, to remove fat from that location.

Figure 30:
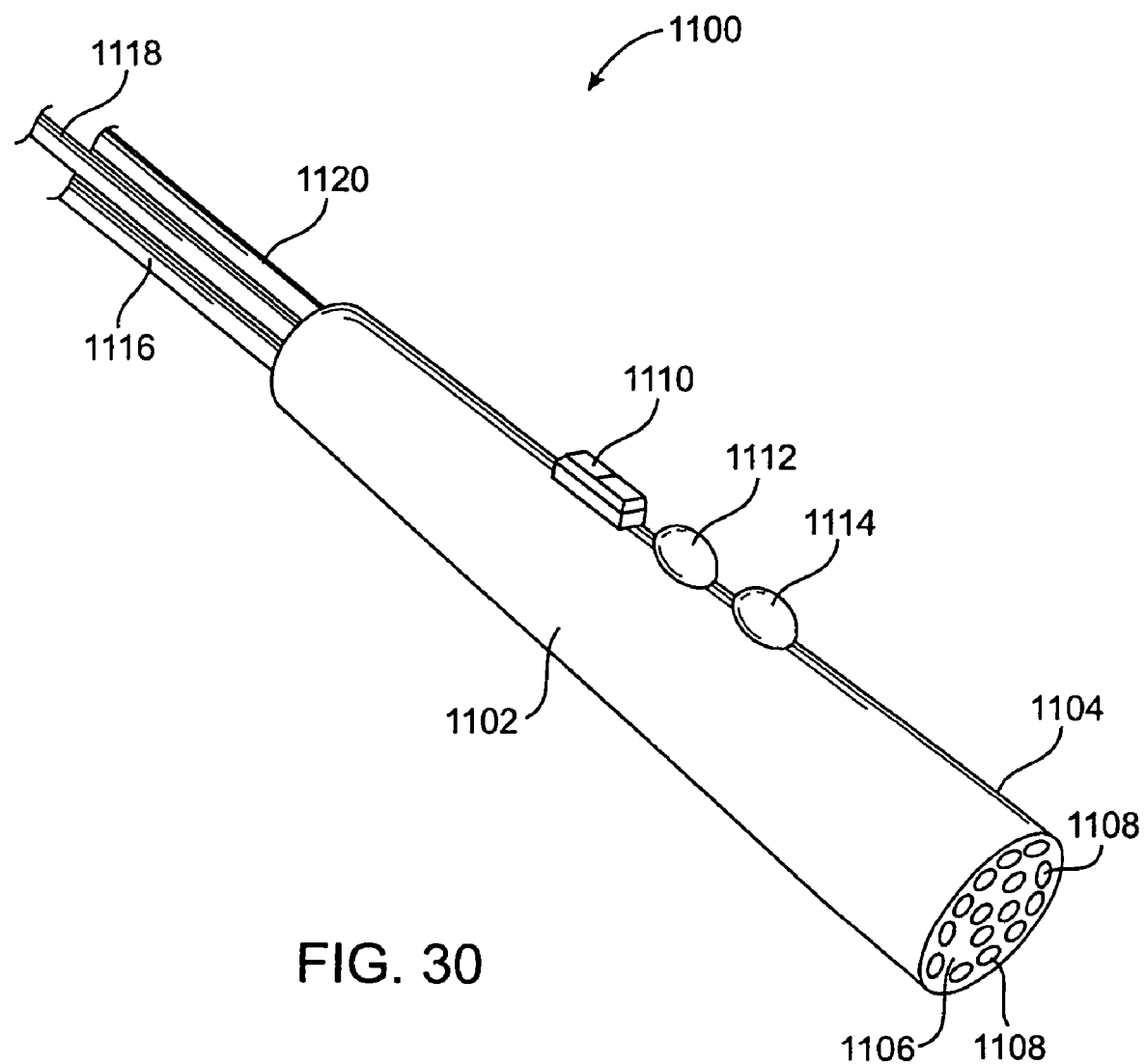
FIG. 30 illustrates a perspective view of an eleventh exemplary embodiment in accordance with the present invention.
Figure 31:
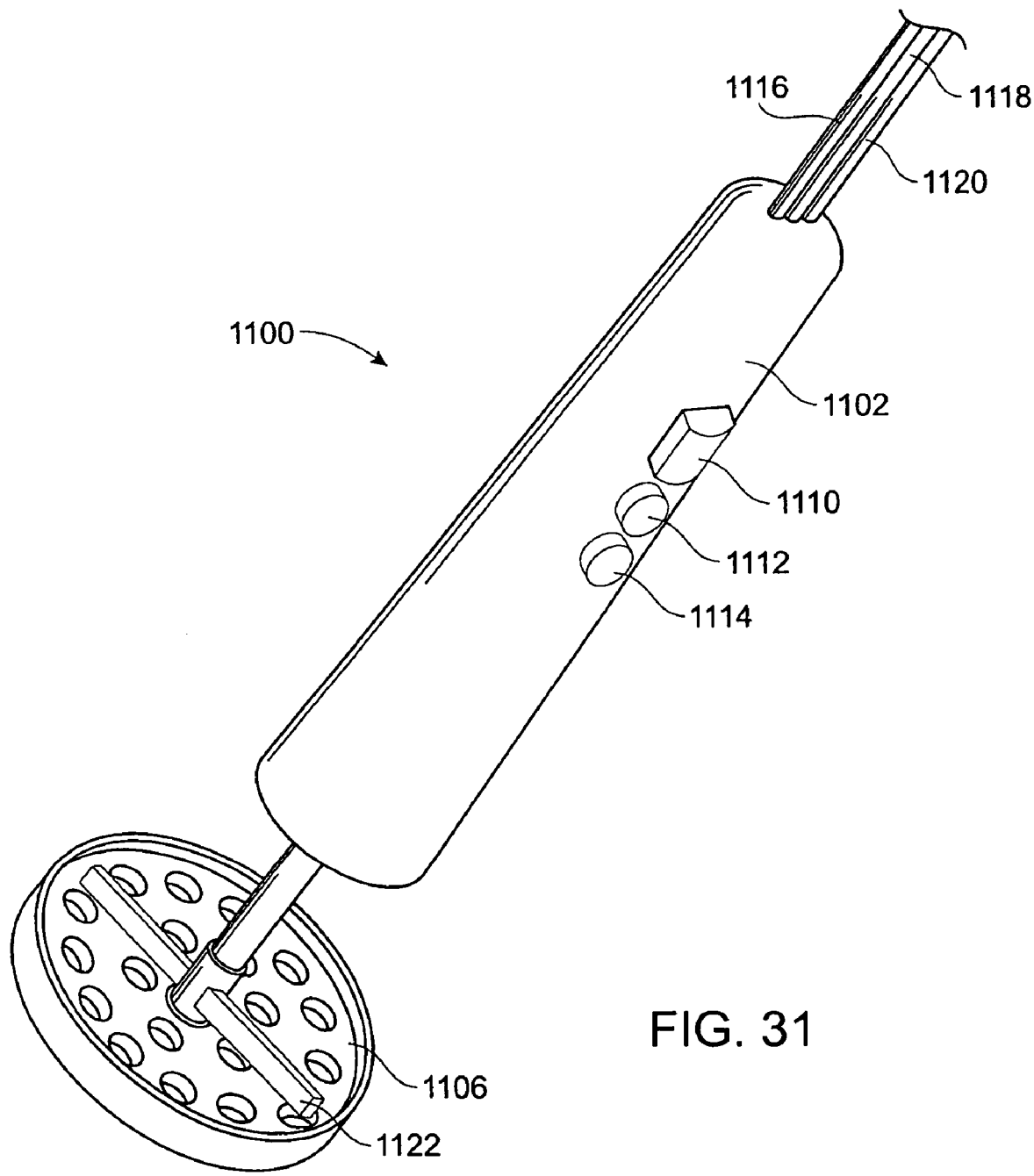
FIG. 31 illustrates a perspective view of the device of FIG. 30, with portions broken away.

FIGS. 30 and 31 schematically illustrate views of an eleventh exemplary embodiment of a fat removal and nerve protection device 1100 in accordance with the present invention. Device 1100 includes a handle 1102 configured to be easily grasped by the hand of a practitioner. Distal end 1104 of handle 1102 includes a screen 1106 having at least one, and preferably a plurality of passages or holes 1108 therethrough. Passages 1108 fluidly communicate the exterior of handle 1102 with the interior thereof. Handle 1102 further includes control switches 1110, 1112, and 1114, for selectively controlling the flow of fluid through irrigation conduit 1116, aspiration conduit 1118, and power through cable 1120. A motor (not illustrated) is provided in handle 1102.

FIG. 31 illustrates handle 1102 with the distal portions of the handle broken away to expose blade 1122 which is rotatably carried in handle 1102. Blade 1122 is similar to blades 322, 410, and 510, described in greater detail above. Blade 1122 may optionally be constructed as an electrocautery device, also described in greater detail above, for which an additional control switch (not illustrated) on handle 1102 would be provided.

The function of device 1100 will now be described with reference to FIGS. 30 and 31. An organ which has a fatty tissue layer is exposed by, e.g., thorachotomy. A practitioner grasps wand handle 1102 in a hand, and presses screen 1106 against the surface of the fat to be removed. By activating the switch fat is thereby caused to extrude through the passages 1022. The practitioner then selectively presses control switches 1110, 1112, and 1114 to selectively irrigate the inner surface of screen 1106, aspirate any fat which has been extruded through the screen, and rotate blade 1122 to cut fat which has been extruded through the screen. Optionally, power is supplied to an electrocautery element (not illustrated) in device 1100, which preferably is blade 1122, to cauterize the capillary bed of the fatty tissue. When a sufficient amount of fat has been removed, the practitioner moves handle 1102 to another site, and presses screen 1122 against the fat.

Figure 32:
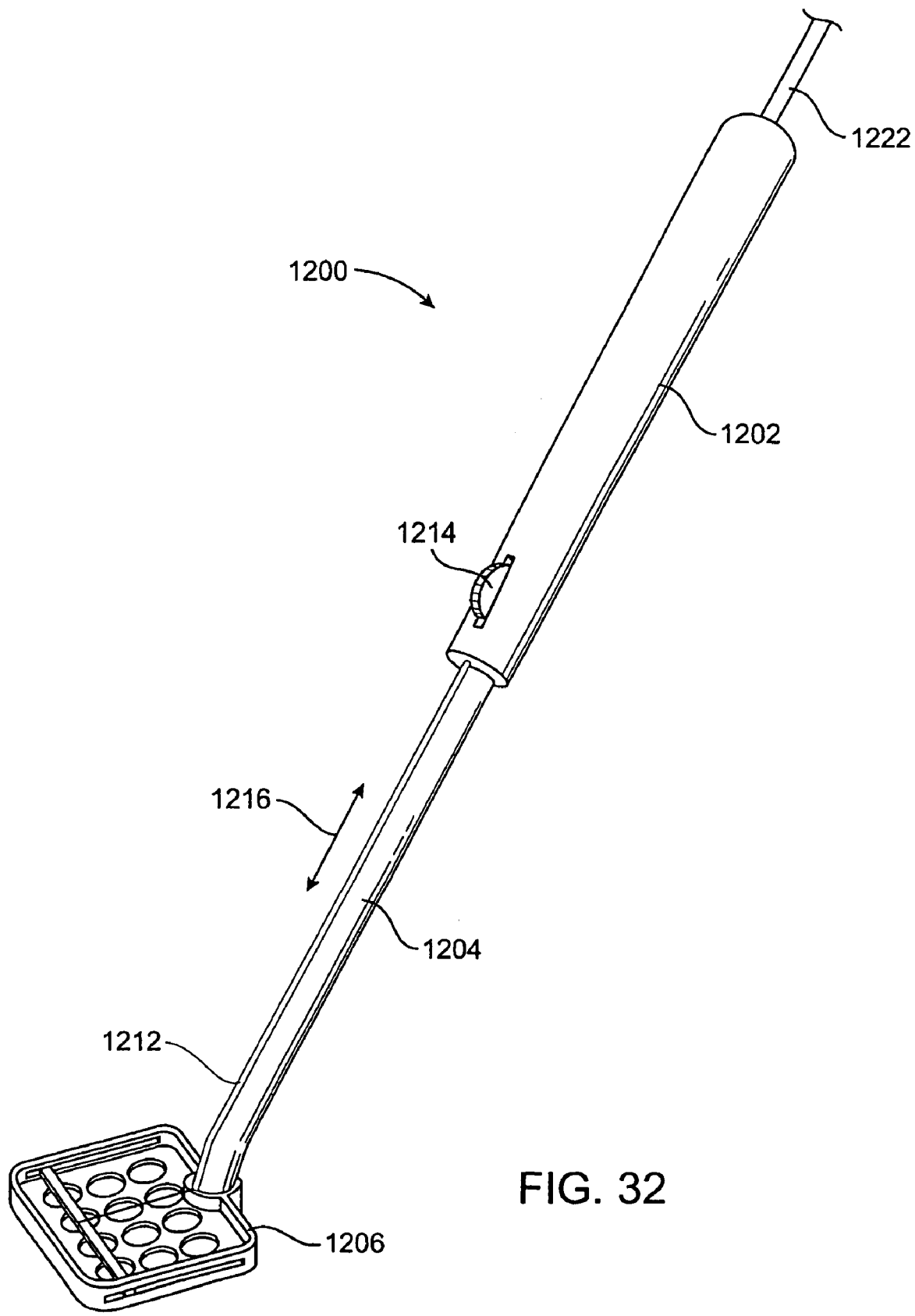
FIG. 32 illustrates a perspective view of a twelfth exemplary embodiment in accordance with the present invention.
Figure 33:
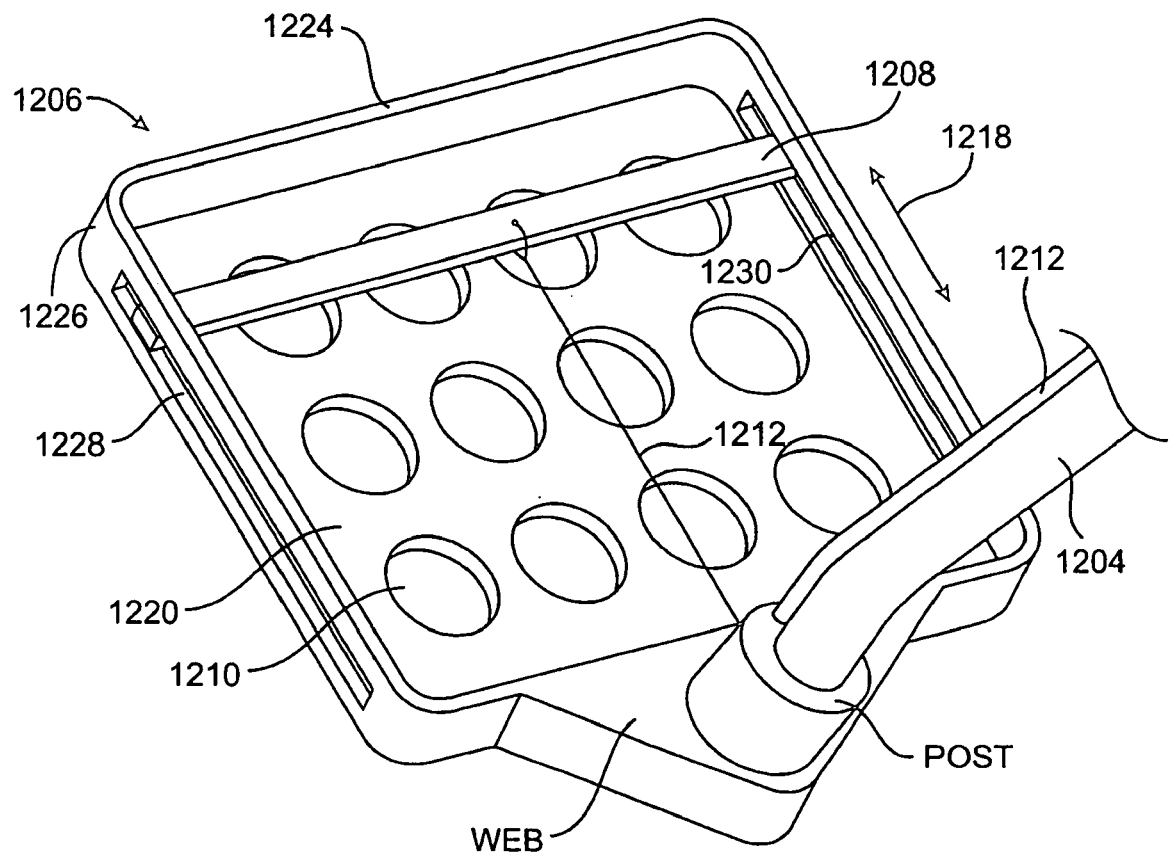
FIG. 33 illustrates an enlarged perspective view of portions of the embodiment illustrated in FIG. 32.

FIGS. 32 and 33 schematically illustrate views of a twelfth exemplary embodiment of a fat removal and nerve protection device 1200 in accordance with the present invention. Device 1200 includes a handle 1202 configured to be easily grasped by the hand of a practitioner. An extension 1204 extends distally from handle 1202 and connects to a plate 1206. Plate 1206 is preferably constructed very similar to plate 1024 described above with reference to FIGS. 27-29, with several differences described in greater detail below.

An electrocautery wire 1208 is provided in device 1200 to cut fat tissue that extrudes through the holes 1210 in plate 1206, in a fashion similar to the embodiments described above. Wire 1208 is connected to an actuator 1212 which extends proximally up through or along the exterior of extension 1204 and into handle 1202. A slidable control member 1214 is attached to actuator 1212, and extends from an interior of handle 1202 (not illustrated) so that a practitioner can slide actuator 1212 proximally and distally along the handle, as indicated by arrow 1216. Proximal and distal movement of actuator 1212 causes wire 1208 to move back and forth, as indicated by arrow 1218, in and along a top surface 1220 of plate 1206. Actuator 1212 preferably is formed of an electrically conductive material, or includes an electrical conductor (not illustrated) therein. A power lead 1222 is connected to a proximal portion of actuator 1212 so that electric power transmitted from the power lead is transmitted to wire 1208. It is to be understood that although heater 1208 may be a "wire" it's shape is not so limited. Rather, any moveable heated element that may be slid or moved over the surface of top surface 1220 may be used. In optional aspects, heater 1208 could be a nickel-chromium wire with current running therethrough, causing it to act as a resistive heater. Other resistive materials could also be used in heater 1208. In alternate embodiments, RF energy (or coherent and incoherent light) could also be used to generate heat within moveable heater 1208.

In preferred aspects, moveable heater 1208 is slid back and forth over the top of plate 1206, thereby cutting the fat projecting through holes 1210. This back and forth movement of heater 1208 across plate 1206 can be repeated as necessary until the nerve or other tissue can be seen without the covering fat. Heater 1208 thus serves both to partially liquefy the fat and to cauterize the small blood vessels within the fat to prevent bleeding from obscuring the view of the nerve.

In optional preferred aspects of the present invention, plate 1206 has thermally insulating characteristics such that nerves are insulated from unwanted heating caused by the heater 1208. For example, plate 1206 may optionally be made of a material such as Lexan®, or other polycarbonate material, or polyfluorinated materials such as Teflon®.

FIG. 33 illustrates an enlarged perspective view of portions of device 1200. Plate 1206 includes a recessed top surface 1220 in which holes 1210 are formed. The size and placement of holes 1210 are substantially similar to the size and placement of passages 1022 in screen 1020, described above with reference to FIGS. 27-29. Plate 1206 includes a raised edge 1224 which preferably extends around the entire periphery of the plate. A sidewall 1226 extends between edge 1224 and surface 1220. A pair of slots 1228, 1230 are formed into sidewall 1226, which receive the ends of wire 1208. Wire 1208 thus can slide in slots 1228, 1230 back and forth, as indicated by arrow 1218, in and along top surface 1220 of plate 1206. As, illustrated in FIG. 33, actuator 1212 extends through extension 1204, through edge 1224, through sidewall 1226, and connects to wire 1208. In accordance with yet another embodiment of the present invention (not illustrated), actuator 1212 can extend along an outer surface of extension 1204. Optionally, actuator 1212 can be to wire 1208 by a pulley (not illustrated).

The function of device 1200 will now be described with reference to FIGS. 32 and 33. An organ which has a fatty tissue layer is exposed by, e.g., thorachotomy. A practitioner grasps handle 1202, and presses plate 1206 against the surface of the fat. Fat is thereby caused to extrude through holes 1210. The practitioner then slides control member 1214 and slides wire 1208 across surface 1220 to simultaneously scrape the fat away and cauterize the capillary bed in the fatty tissue. If desired, wire 1208 may be used without application of energy to the loop. When a sufficient amount of fat has been wiped away from a particular site, device 1200 is moved to another location on the organ, e.g., heart, to remove fat from that location.

Figure 34:
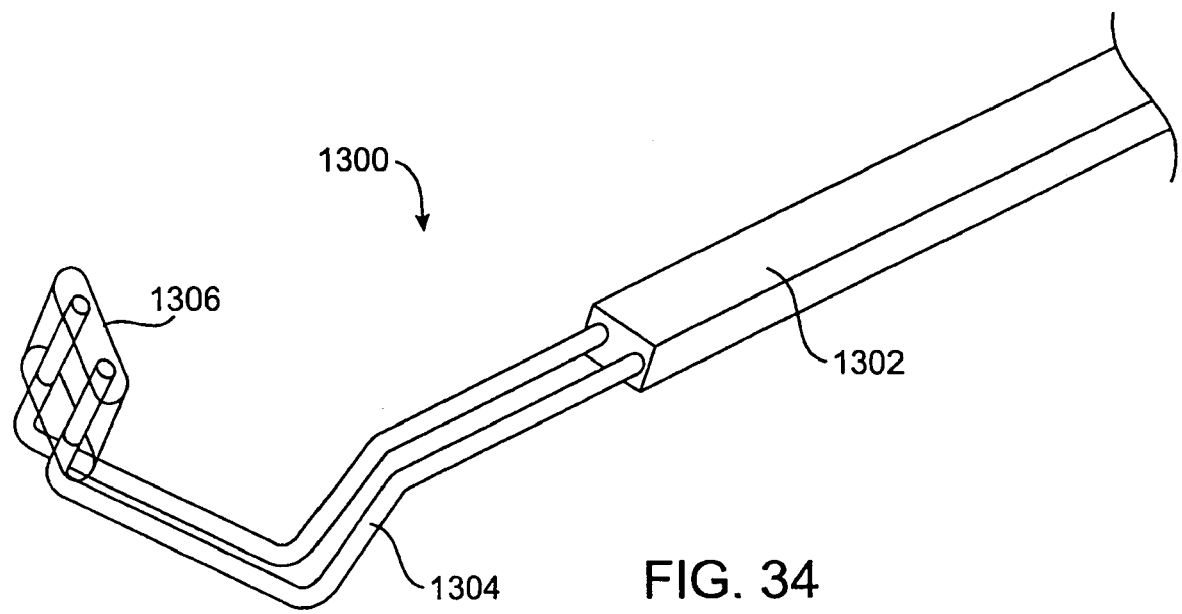
FIG. 34 illustrates a bipolar RF device for removal of fat for open chest procedures according to yet further aspects of the present invention.
Figure 35:
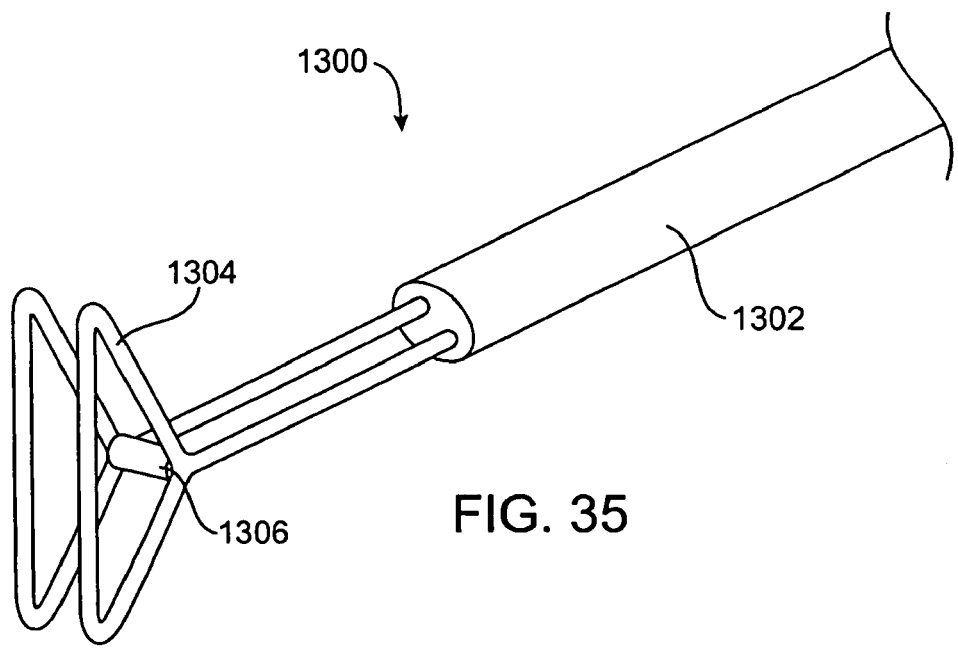
FIG. 35 illustrates another bipolar RF device for removal of fat for open chest procedures.

FIGS. 34 and 35 schematically illustrate views of a thirteenth exemplary embodiment of a bipolar radio frequency fat removal device 1300 in accordance with the present invention. Device 1300 includes a handle 1302, two identical bi-polar electrodes 1304, and a spacer bar 1306. The bi-polar electrodes 1304 can be made any shape, including straight electrodes to fit the contour of the surface they are to be applied to. It has been found that an efficacious electrode has a wire diameter of about 0.015-0.045 inches, with a preferable wire diameter of 0.031 inches, and that the electrodes be spaced apart from about 0.040 to about 0.200 inches, with a preferable spacing of 0.080 inches, from the centerline of one wire to the centerline of the other wire. A high impedance (e.g., 500 to 2500 ohms) RF generator is used to apply power between the two electrodes 1304 through the fat in the immediate area, thereby melting the fat. If needed, a nerve/artery/vein guard, such as that shown in FIGS. 27-29, can be used for their protection. If further desired, an aspiration device can be used to collect the melted fat, as will be readily appreciated by one of skill in the art.

Figure 36A:
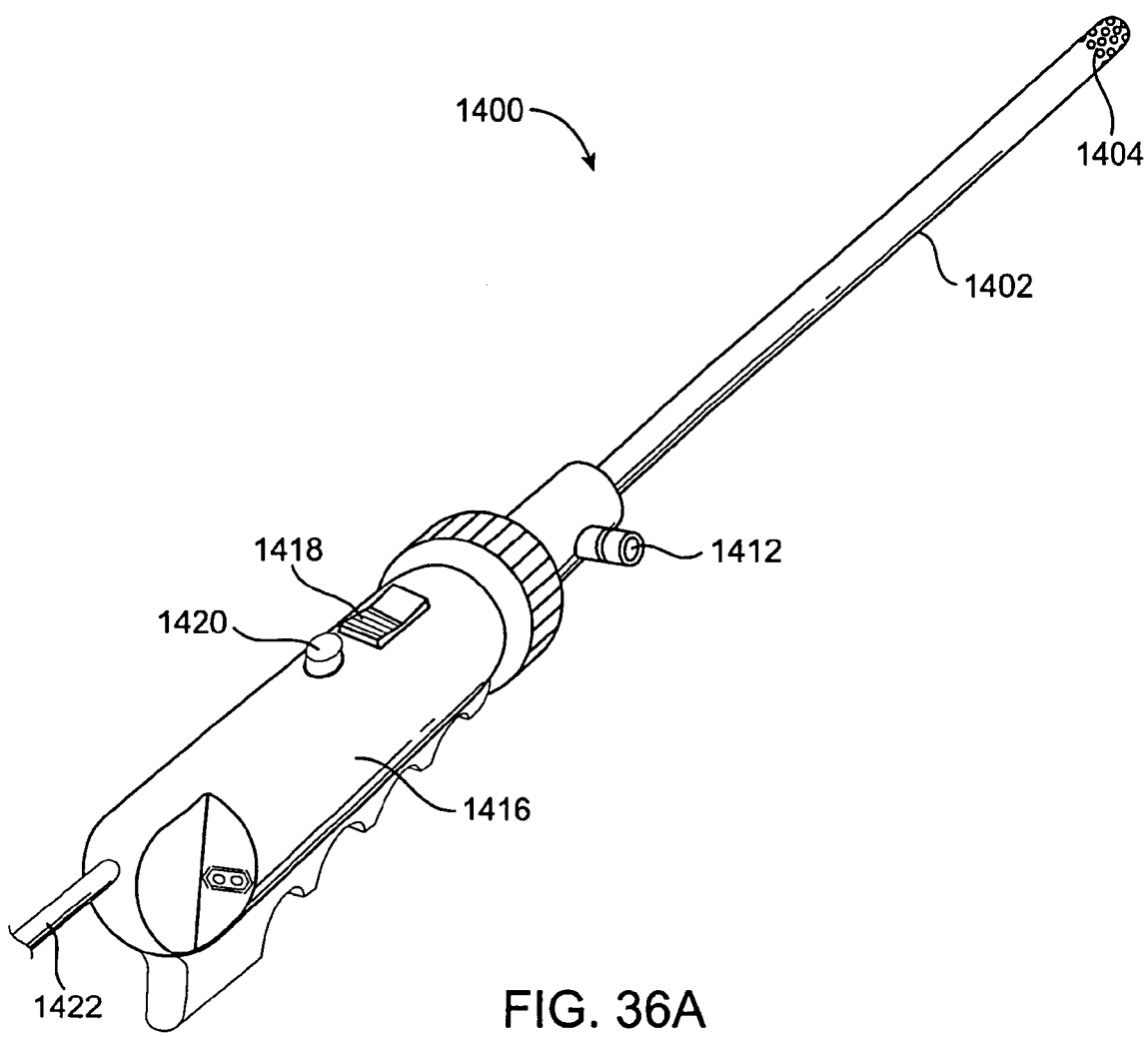
FIGS. 36A, B and C illustrate bipolar wire electrodes that rotate within a sheath for transthoracic procedures.
Figure 36B:
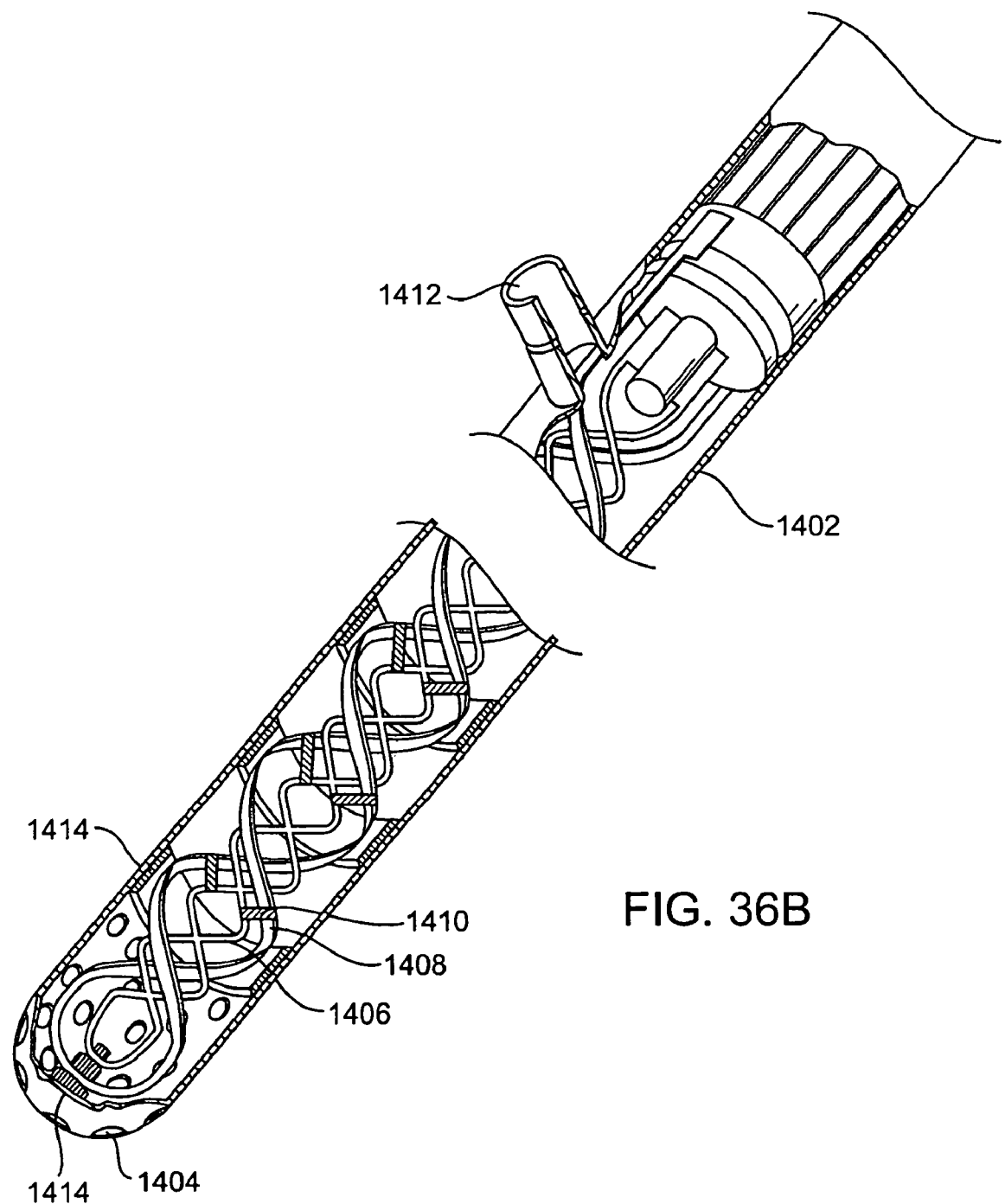
Figure 36C:
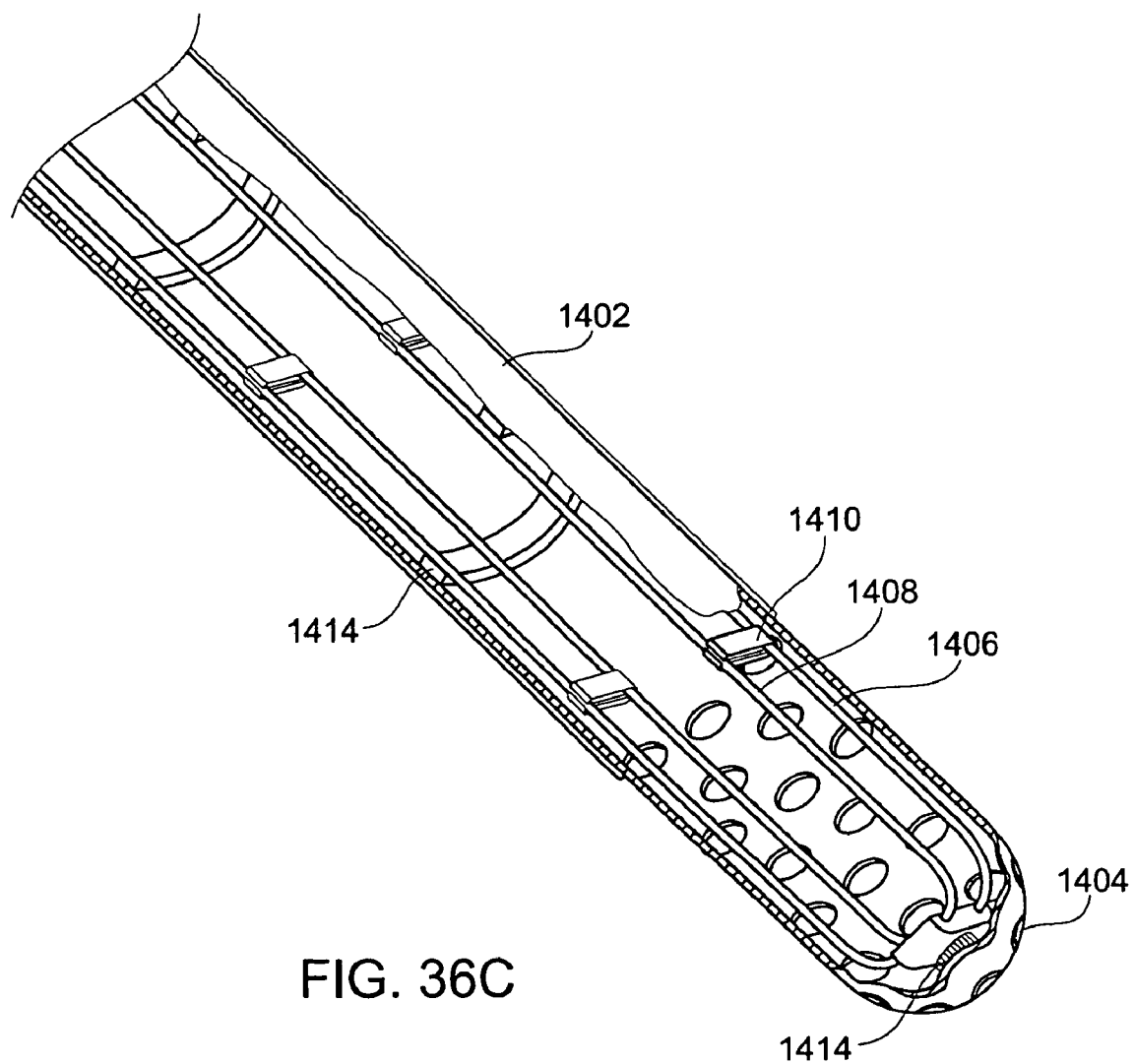

FIGS. 36A, B and C illustrate a fourteenth exemplary embodiment of a bipolar radio frequency fat removal device 1400 which includes a shaft 1402 with distal holes 1404 that is placed through a thoracotomy by the proximal handle 1416 with an on/off switch 1418, power on/off light indicator 1420, a vacuum port 1412, and RF power connection 1422. FIG. 36B again illustrates the sheath 1402 with distal tip holes 1404 for fat to enter and bipolar electrodes 1406 and 1408 being rotating wireforms evenly spaced apart by spacers 1410. The wireform bipolar electrodes of preferable diameters between about 0.015 to 0.045 inches, with a more preferable diameter of 0.031, one spaced inside the other at a centerline to centerline distance from 0.040 to 0.2000 inches, with a preferable distance of 0.080 inches, are formed in a spiral or helical configuration and rotated in such a fashion to move the melted fat to the proximal end of the device for removal through a vacuum port 1412. FIG. 36C illustrates the same device as in FIG. 36B, except the electrodes 1406 and 1408 are positioned beside each other at the same spacing as in FIG. 36B. The proximal, handle end of the device is constructed to mate with a rotating mechanism with rotating seals such that the wire form electrodes are rotated as a unit and held in position relative to the outer sheath by spacers 1414. Notably, the wireforms only need to extend slightly beyond the holes 1404 and from there back to the proximal end of the device can be of any form or configuration as long as the spacing between the electrodes is maintained. It should also be noted that in the preferred embodiment the holes 1404 in FIGS. 36A, B and C would extend only 180 degrees of the 360 degrees around the axis of the sheath 1408.

The function of the device in FIGS. 36A, B and C will now be described. Using the handle 1416 the sheath 1402 is pushed through the thoracotomy until the distal tip 1404 is pressed against the fat. The suction, RF power and inner electrodes rotating motor are turned on and the distal tip 1404 positioned over the area of fat to be removed and advanced as the fat is melted away and removed from the area by the vacuum.

Figure 37A:
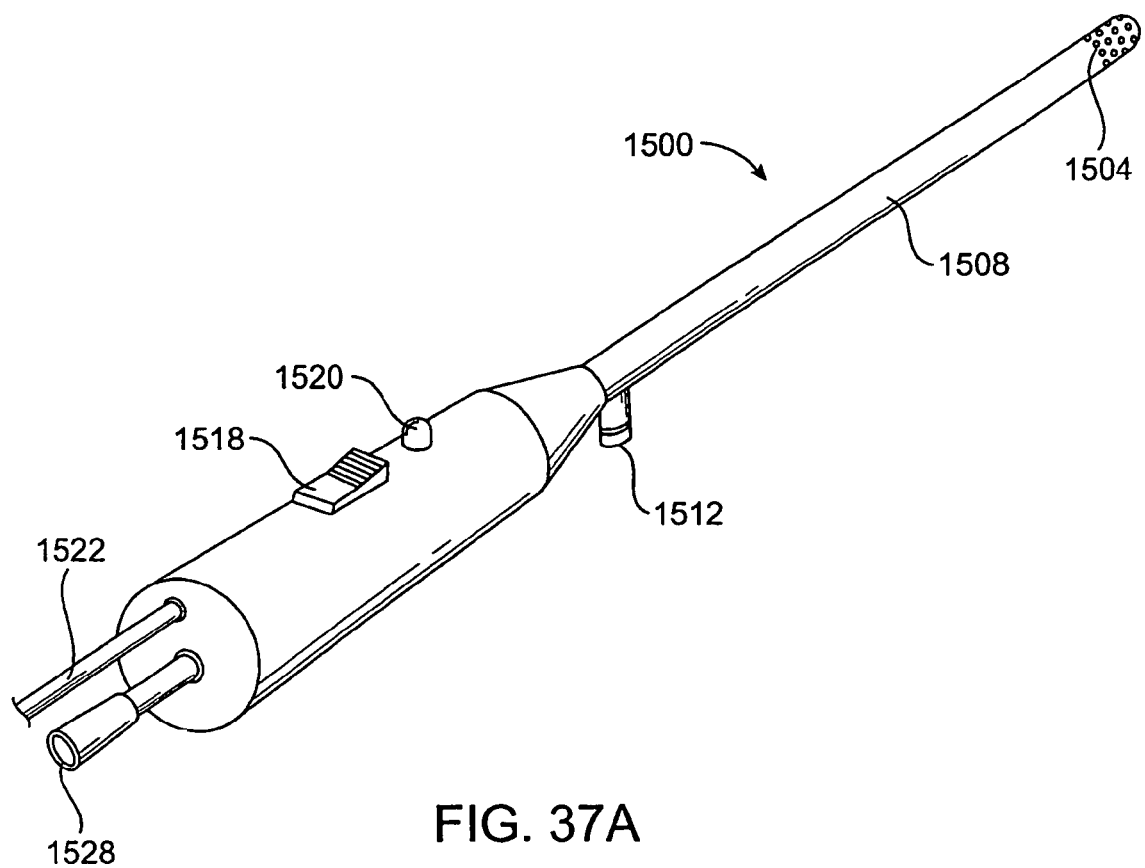
FIGS. 37A, B, C and D illustrate a device with one of the bipolar electrodes being the outer sheath and the other being an electrode that rotates relative to the other electrode also with the potential of an auger type device to move the melted fat from the distal to the proximal end of the device.
Figure 37B:
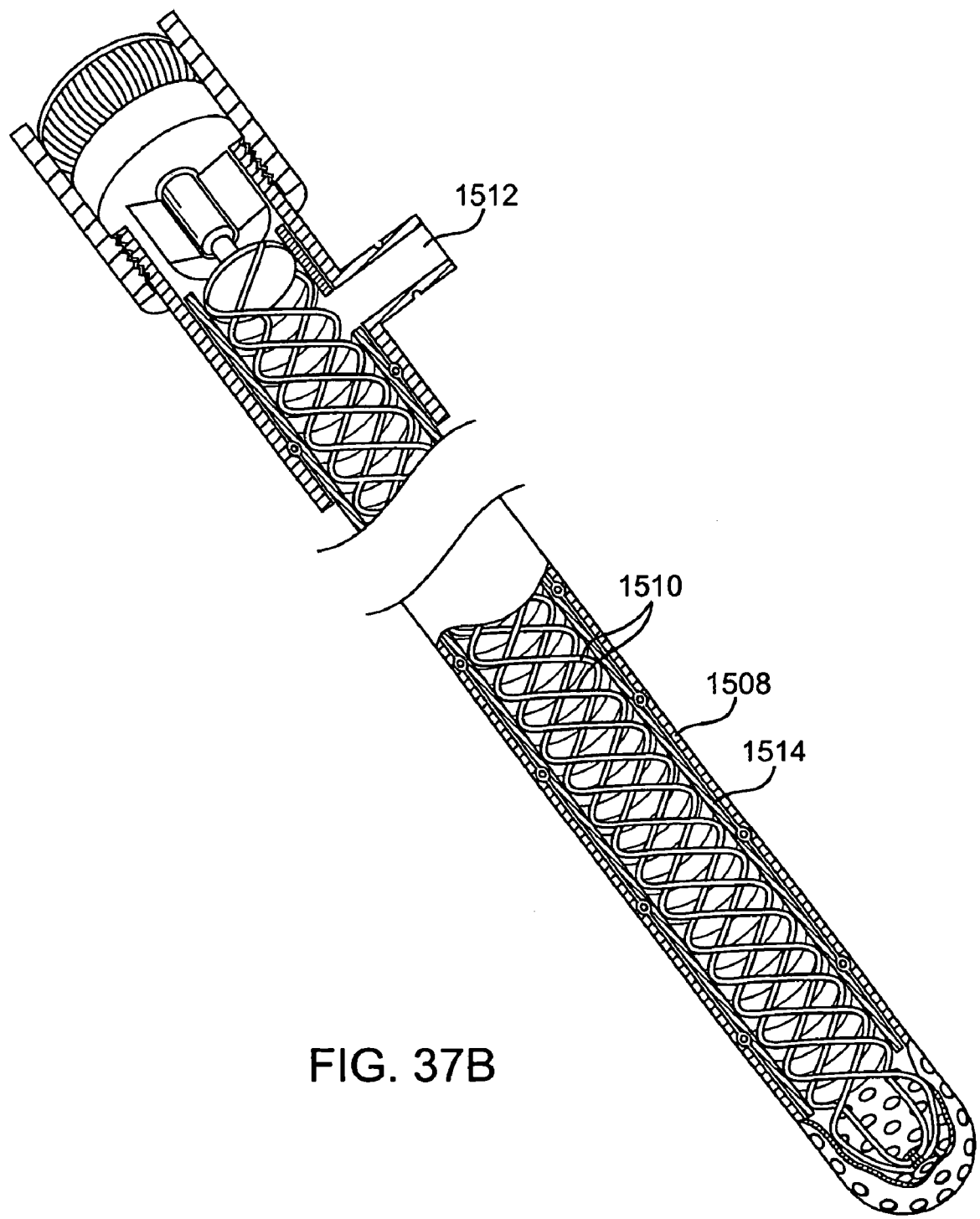
Figure 37C:
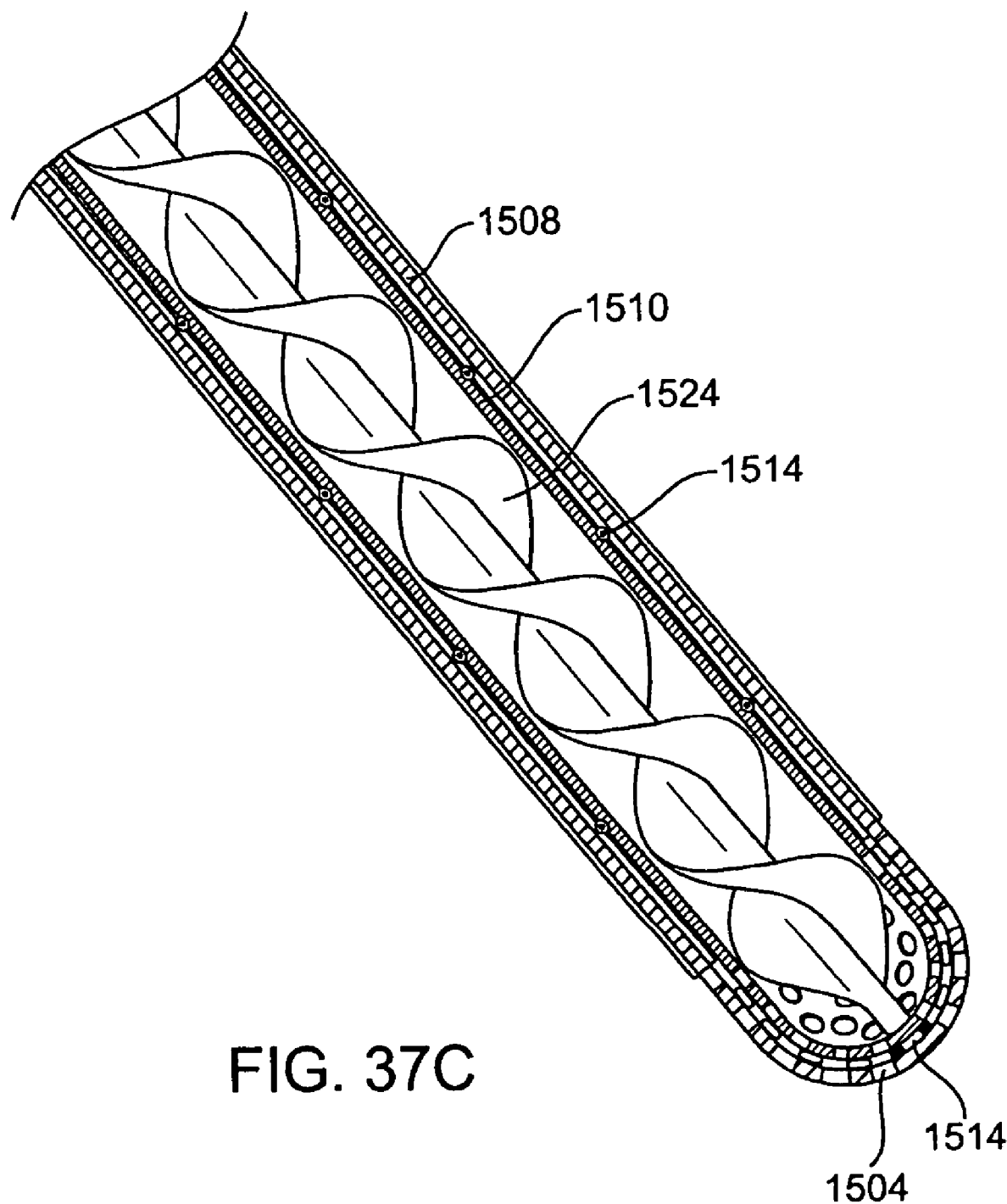
Figure 37D:
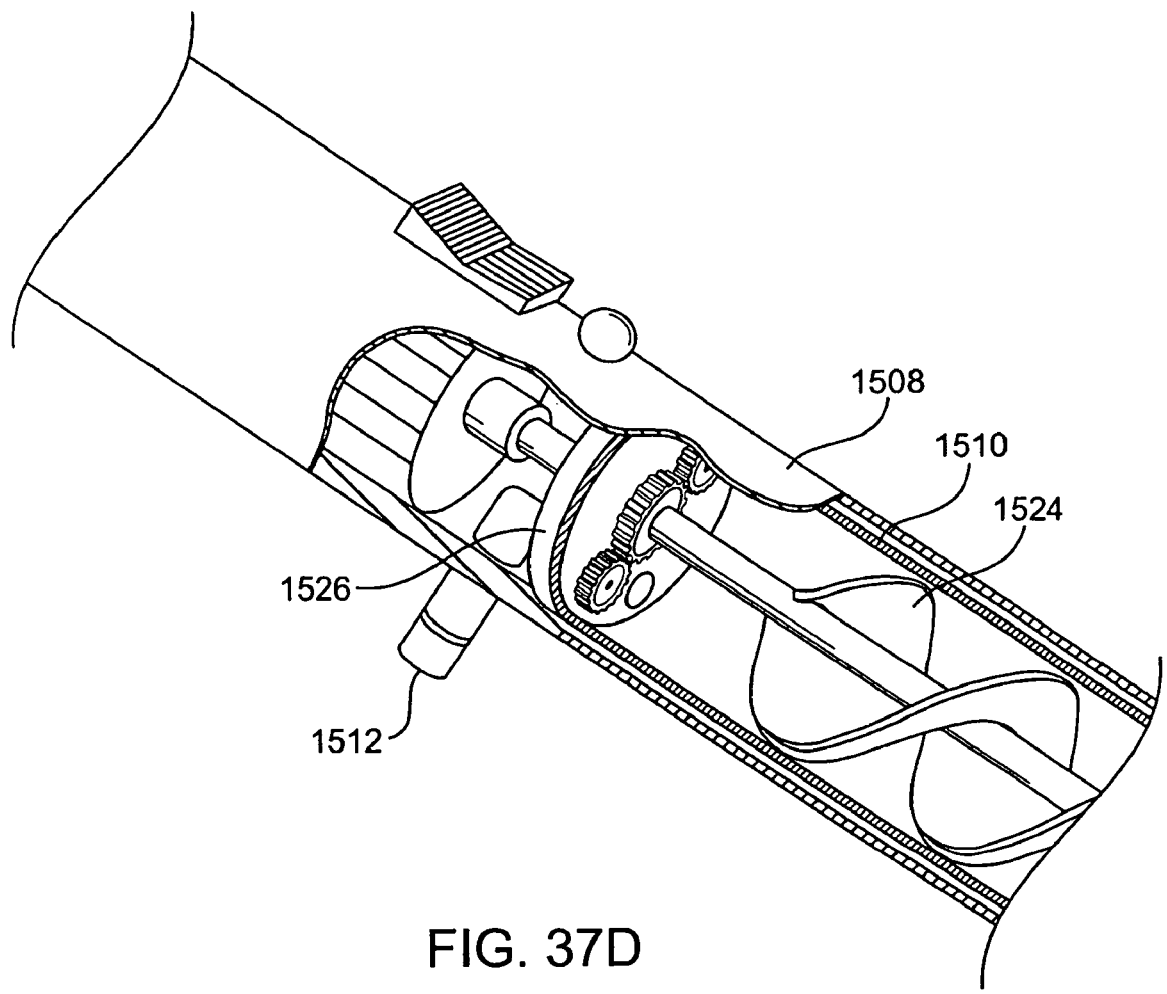

FIGS. 37A, B, C, and D illustrate a fifteenth embodiment of a bipolar radio frequency fat removal device 1500 similar to the fourteenth embodiment except as shown by FIGS. 37B and C. The outer sheath 1508, which includes distal holes 1504, is used as one of the electrode and there is a single rotating inner electrode 1510 of wireform or solid form with spacers 1514 maintaining the required spacing between the electrodes, and there is an inner auger 1524 in FIG. 37C which is rotated to move the fat from the distal to the proximal end of the device. FIG. 37D illustrated a gear box that rotates the inner electrode 1510 relative to the outer electrode 1508, and rotates the auger 1524 relative to the inner electrode 1510 to optimize melting and movement of the fat to the exit vacuum port 1512. Item 1528 in FIG. 37A will be explained in the discussion of FIG. 38. It should also be noted that in the preferred embodiment the holes 1504 in FIGS. 37A, B and C would extend only 180 degrees of the 360 degrees around the axis of the sheath 1508.

The functions of the device in FIGS. 37A, B, C and D are generally the same as in FIGS. 36A, B and C except there is a gear box to rotate only one inner electrode and in addition there is a rotating auger to move the fat from the distal tip to the proximal end of the sheath and out the vacuum port.

Figure 38A:
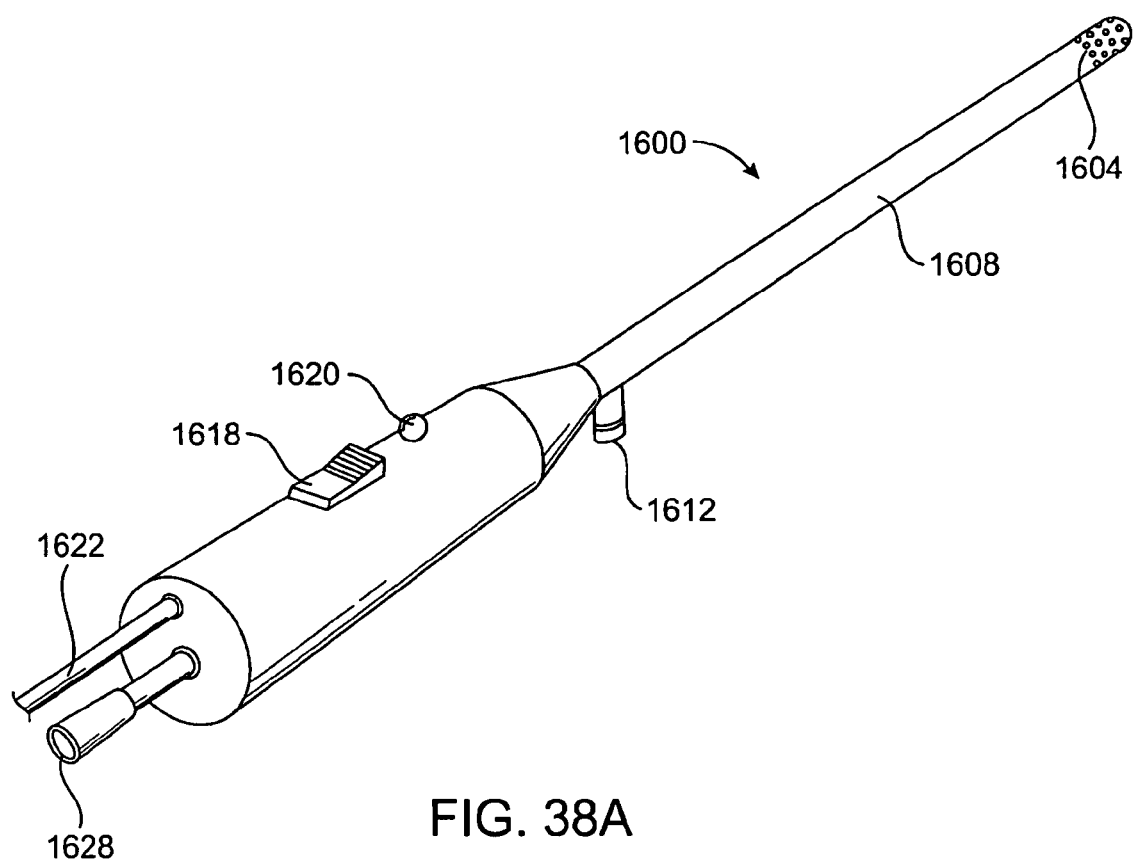
FIGS. 38A and B illustrate a device similar to the device in FIG. 37 with a central lumen to accept an endoscope for viewing the area of treatment or a therapeutic device like a lead attachment device.
Figure 38B:
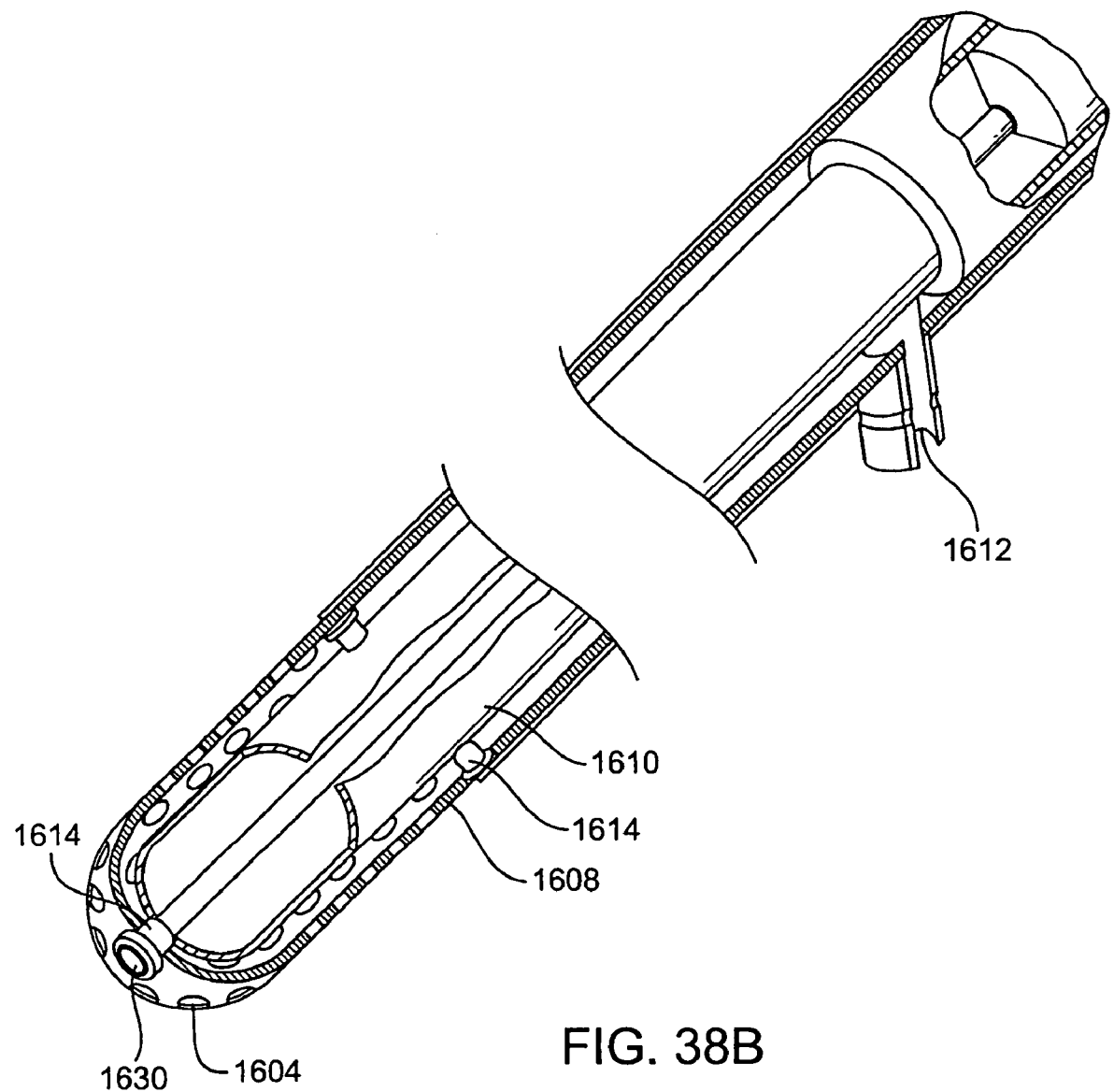

The sixteenth embodiment depicted by FIGS. 38A and B is similar to embodiments fourteenth and fifteenth illustrated by FIGS. 36 and 37, except there is a central lumen 1630 starting at the distal tip and running axially to the proximal outlet 1628 allowing for use of an endoscope to view the area being treated and/or to provide a conduit for a therapeutic device such as pacing lead attachment or other desired therapeutic procedures. In this version, the fat enters holes 1604 and is melted by bipolar electrodes 1608 and 1610, evenly spaced by spacer 1614, and the melted fat travels between the two bipolar electrodes to the proximal end and out the vacuum port 1612. Further optionally, the device may include holes in the inner electrode 1610 for transmission of the melted fat from the distal tip to the vacuum port via a proximal hole in electrode 1610 communicating with vacuum port 1612. Rotation of the inner electrode relative to the outer electrode may alternatively be performed in accordance with the present invention. In a preferred embodiment, the holes 1604 in FIGS. 38A, B, and C would extend only 180 degrees of the 360 degrees around the axis of the sheath 1608.

The function of the device in FIGS. 38A and B is similar to the two previously described devices, with the exceptions that there is a lumen along the axis of the device to accept a angioscope to view the area being treated or a therapeutic device to treat the area, attach diagnostic or pacing leads, etc. This device can, but does not have to, have a moving inner electrode.

While the invention has been described in detail with reference to preferred embodiments thereof, it will be apparent to one skilled in the art that various changes can be made, and equivalents employed, without departing from the scope of the invention.

What is claimed is:

1. A method of removing fatty tissue while protecting nerves, comprising the steps of:
   exposing a portion of said fatty tissue;
   pressing said fatty tissue with a non-convex surface having at least one hole;
   extruding fat through said at least one hole, the hole being dimensioned to allow fat cells to extrude through while preventing nerves from passing therethrough; and
   cutting, using a blade, fat that has extruded through said hole on a side of said surface opposite said fatty tissue.

2. A method in accordance with claim 1, wherein said step of extruding fat further comprises the step of preventing nerves from passing through said at least one hole while permitting blood vessels to pass therethrough.

3. A method in accordance with claim 1, further comprising cauterizing fat that has extruded through said hole on a side of said surface opposite said fatty tissue.

4. A method in accordance with claim 1, further comprising heating said fatty tissue at a time selected from the group consisting of prior to said cutting step, during said cutting step, and both prior and during said cutting step.

5. A method in accordance with claim 1, wherein said step of pressing said fat layer further comprises pressing with a surface having at least one hole located on a distalmost end of a wand.

6. A method in accordance with claim 1, wherein said step of pressing said fat layer further comprises pressing with a surface having at least one hole located proximal of a distalmost end of a wand.

7. A method in accordance with claim 1, wherein the hole has a diameter R, and said fat is extruded a distance D through the hole having a diameter R, the ratio D/R being about 1.0.

8. A method in accordance with claim 1, wherein the hole has a diameter R, said fat is extruded a distance D through the hole having a diameter R, and D is from 10% less than the diameter of a nerve to be protected to 6 mm.

9. A method in accordance with claim 1, wherein the hole has a diameter R, said fat is extruded a distance D through the hole having a diameter R, and R is from 10% less than the diameter of a nerve to be protected to 6 mm.

10. A method of removing fatty tissue while protecting nerves, comprising the steps of:
    exposing a portion of said fatty tissue;
    pressing said fatty tissue with a non-convex surface having at least one hole;
    extruding fat through said at least one hole, the hole being dimensioned to allow fat cells to extrude through while preventing nerves from passing therethrough; and
    cutting, using a shearing member, fat that has extruded through said hole on a side of said surface opposite said fatty tissue.

11. A method in accordance with claim 10, wherein said step of extruding fat further comprises the step of preventing nerves from passing through said at least one hole while permitting blood vessels to pass therethrough.

12. A method in accordance with claim 10, further comprising cauterizing fat that has extruded through said hole on a side of said surface opposite said fatty tissue.

13. A method in accordance with claim 10, further comprising heating said fatty tissue at a time selected from the group consisting of prior to said cutting step, during said cutting step, and both prior and during said cutting step.

14. A method in accordance with claim 10, wherein said step of pressing said fat layer further comprises pressing with a surface having at least one hole located on a distalmost end of a wand.

15. A method in accordance with claim 10, wherein said step of pressing said fat layer further comprises pressing with a surface having at least one hole located proximal of a distalmost end of a wand.

16. A method in accordance with claim 10, wherein the hole has a diameter R, and said fat is extruded a distance D through the hole having a diameter R, the ratio D/R being about 1.0.

17. A method in accordance with claim 10, wherein the hole has a diameter R, said fat is extruded a distance D through the hole having a diameter R, and D is from 10% less than the diameter of a nerve to be protected to 6 mm.

18. A method in accordance with claim 10, wherein the hole has a diameter R, said fat is extruded a distance D through the hole having a diameter R, and R is from 10% less than the diameter of a nerve to be protected to 6 mm.

19. A method of removing fatty tissue while protecting nerves, comprising the steps of:
    exposing a portion of said fatty tissue;
    pressing said fatty tissue with a non-convex surface having at least one hole;
    extruding fat through said at least one hole, the hole being dimensioned to allow fat cells to extrude through while preventing nerves from passing therethrough; and
    cutting, using a scraper, fat that has extruded through said hole on a side of said surface opposite said fatty tissue.

20. A method in accordance with claim 19, wherein said step of extruding fat further comprises the step of preventing nerves from passing through said at least one hole while permitting blood vessels to pass therethrough.

21. A method in accordance with claim 19, further comprising cauterizing fat that has extruded through said hole on a side of said surface opposite said fatty tissue.

22. A method in accordance with claim 19, further comprising heating said fatty tissue at a time selected from the group consisting of prior to said cutting step, during said cutting step, and both prior and during said cutting step.

23. A method in accordance with claim 19, wherein said step of pressing said fat layer further comprises pressing with a surface having at least one hole located on a distalmost end of a wand.

24. A method in accordance with claim 19, wherein said step of pressing said fat layer further comprises pressing with a surface having at least one hole located proximal of a distalmost end of a wand.

25. A method in accordance with claim 19, wherein the hole has a diameter R, and said fat is extruded a distance D through the hole having a diameter R, the ratio D/R being about 1.0.

26. A method in accordance with claim 19, wherein the hole has a diameter R, said fat is extruded a distance D through the hole having a diameter R, and D is from 10% less than the diameter of a nerve to be protected to 6 mm.

27. A method in accordance with claim 19, wherein the hole has a diameter R, said fat is extruded a distance D through the hole having a diameter R, and R is from 10% less than the diameter of a nerve to be protected to 6 mm.

* * * * *